US012398848B2

(12) United States Patent
Medricky

(10) Patent No.: US 12,398,848 B2
(45) Date of Patent: Aug. 26, 2025

(54) WHITE LIGHT LUMINAIRE FOR EVERYDAY ACTIVITIES THAT REGENERATES THE RETINA OF THE EYE IN REAL TIME, DAMAGED BY BLUE LIGHT

(71) Applicants: Hynek Medricky, Prague (CZ); Daniel Jesensky, Prague (CZ); Daniel Stepan, Prague (CZ)

(72) Inventor: Hynek Medricky, Prague (CZ)

( * ) Notice: Subject to any disclaimer, the term of this patent is extended or adjusted under 35 U.S.C. 154(b) by 0 days.

(21) Appl. No.: 18/258,196

(22) PCT Filed: Dec. 16, 2021

(86) PCT No.: PCT/IB2021/061828
§ 371 (c)(1),
(2) Date: Jun. 16, 2023

(87) PCT Pub. No.: WO2022/130268
PCT Pub. Date: Jun. 23, 2022

(65) Prior Publication Data
US 2024/0060606 A1 Feb. 22, 2024

(30) Foreign Application Priority Data
Dec. 17, 2020 (CZ) ................................ CZ2020-688

(51) Int. Cl.
*F21K 9/00* (2016.01)
*A61N 5/06* (2006.01)
(Continued)

(52) U.S. Cl.
CPC .............. *F21K 9/00* (2013.01); *A61N 5/0622* (2013.01); *F21V 9/30* (2018.02);
(Continued)

(58) Field of Classification Search
CPC ............ F21K 9/00; F21K 9/30; A61N 5/0622
See application file for complete search history.

(56) References Cited

U.S. PATENT DOCUMENTS 6,183,086 B1 * 2/2001 Neubert ............... A61B 3/0008
351/221
6,528,954 B1 * 3/2003 Lys ........................ H05B 45/22
315/158

(Continued)

FOREIGN PATENT DOCUMENTS

WO 2011143907 A1 11/2011
WO 2020008397 A1 1/2020

OTHER PUBLICATIONS

International Search Report; issued by Patent Cooperation Treaty on Mar. 14, 2022.
Written Opinion of the International Searching Authority.

*Primary Examiner* — Bryon T Gyllstrom
(74) *Attorney, Agent, or Firm* — CIONICA IP Law P.C.

(57) ABSTRACT

White light luminaire for everyday activities that regenerates the retina of the eye in real time, damaged by blue light, contains at least one blue chip covered by a luminophore with the maximum of the radiated energy at the wavelength λ=670 to 680 nm, whereas the ratio between the blue spectral component from the wavelength range 400 to 490 nm and the green spectral component from the wavelength range 490 to 570 nm is 1:1.6 max., or the ratio between the green spectral component from the wavelength range 490 to 570 nm and the red spectral component from the wavelength range 570 to 780 nm is 1:3 min.

8 Claims, 28 Drawing Sheets

Figures 12A, 12B:
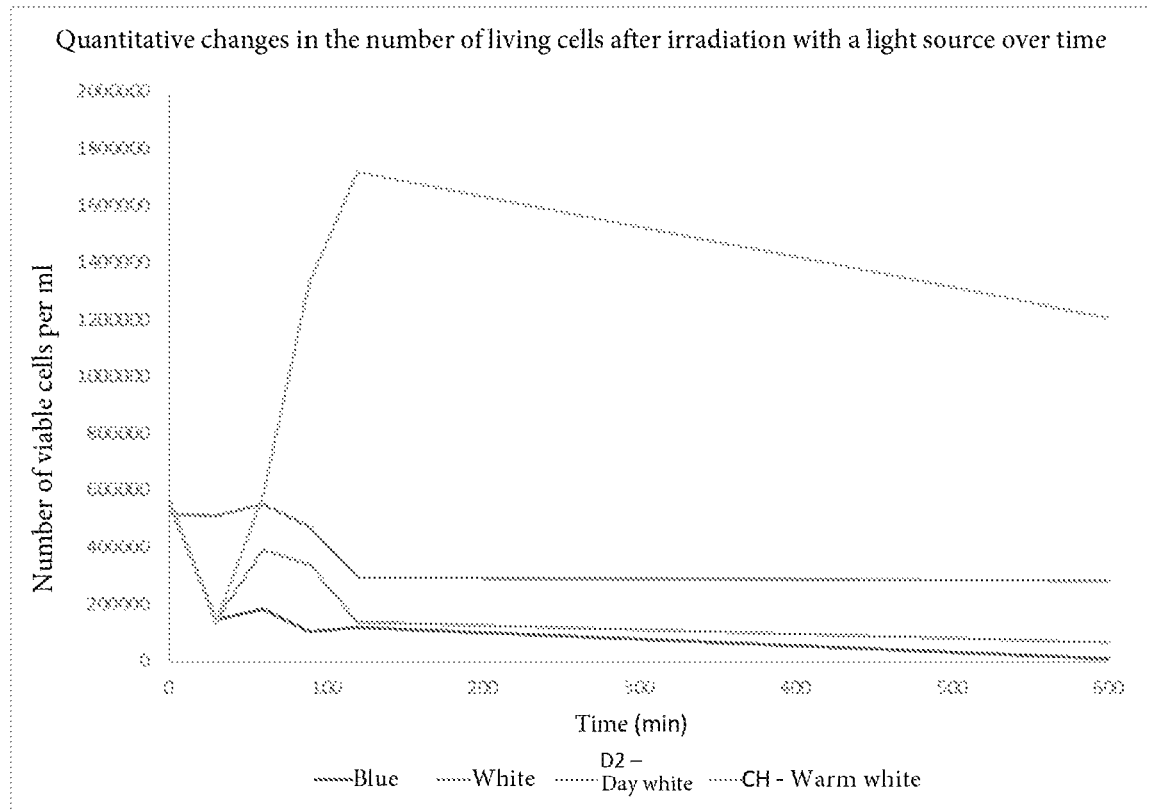

(51) Int. Cl.
*F21V 9/30* (2018.01)
*F21Y 113/13* (2016.01)
*F21Y 115/10* (2016.01)

(52) U.S. Cl.
CPC .............. *A61N 2005/0635* (2013.01); *A61N 2005/0651* (2013.01); *A61N 2005/0663* (2013.01); *F21Y 2113/13* (2016.08); *F21Y 2115/10* (2016.08)

(56) References Cited

U.S. PATENT DOCUMENTS

| | | | | |
|---|---|---|---|---|
| 6,965,205 B2* | 11/2005 | Piepgras | ............... | H05B 45/20 315/318 |
| 7,014,336 B1* | 3/2006 | Ducharme | ............... | F21K 9/20 362/240 |
| 7,135,664 B2* | 11/2006 | Vornsand | ............... | H05B 45/22 250/205 |
| 7,144,131 B2* | 12/2006 | Rains | ............... | F21V 7/26 362/231 |
| 7,161,556 B2* | 1/2007 | Morgan | ............... | H05B 47/175 340/9.16 |
| 11,777,199 B2* | 10/2023 | Bani Hani | ............... | H01Q 21/28 343/721 |
| 2004/0052076 A1* | 3/2004 | Mueller | ............... | F21V 23/0442 362/293 |
| 2004/0105261 A1* | 6/2004 | Ducharme | ............... | F21V 23/045 362/231 |
| 2011/0273107 A1* | 11/2011 | Hsia | ............... | F21K 9/64 315/250 |
| 2012/0226334 A1* | 9/2012 | Gardiner | ............... | A61B 5/395 607/88 |
| 2016/0066384 A1* | 3/2016 | Dias | ............... | H05B 45/20 315/297 |
| 2023/0055346 A1* | 2/2023 | Fortkort | ............... | A61N 5/0622 |

* cited by examiner

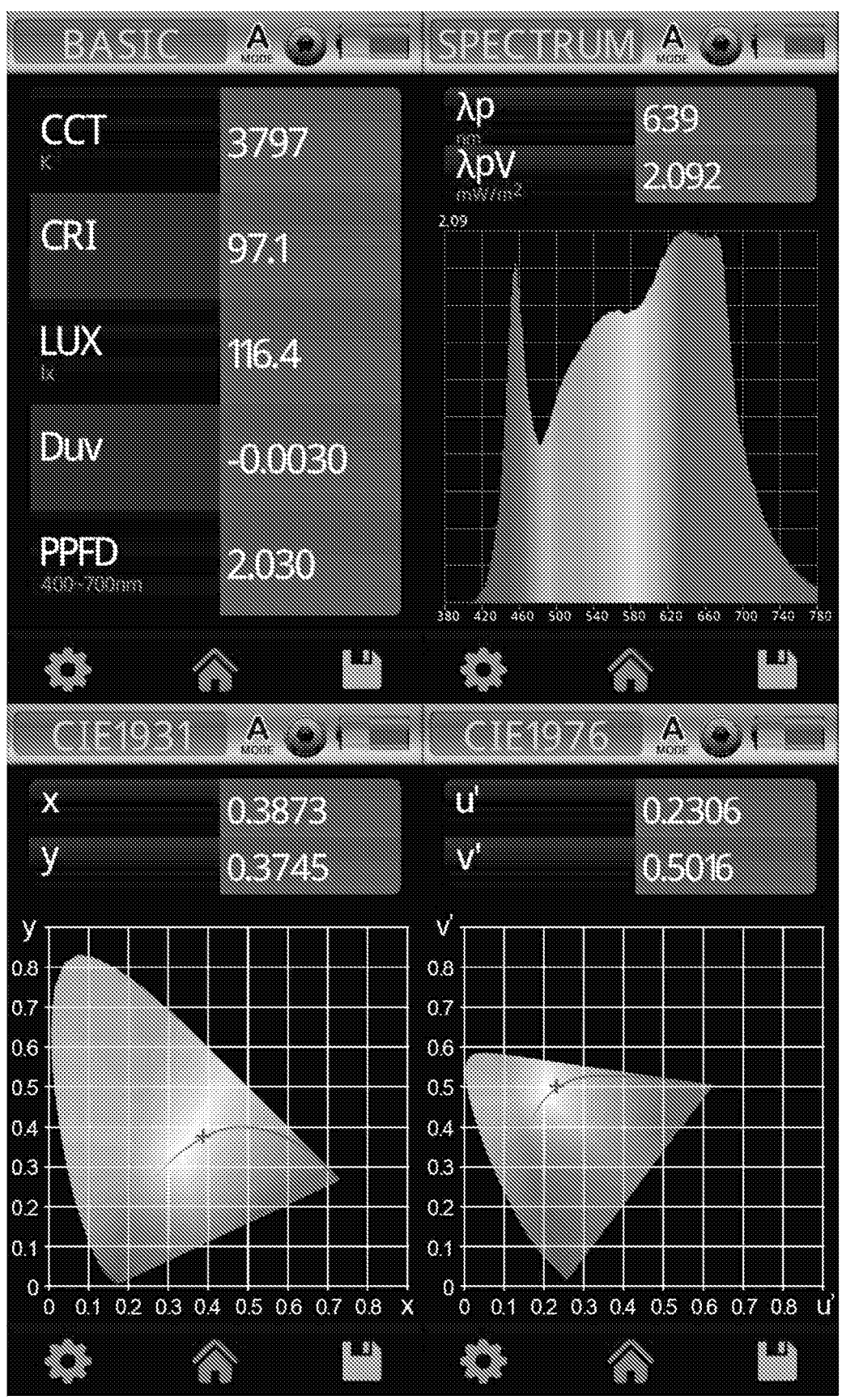
Fig. 1.1

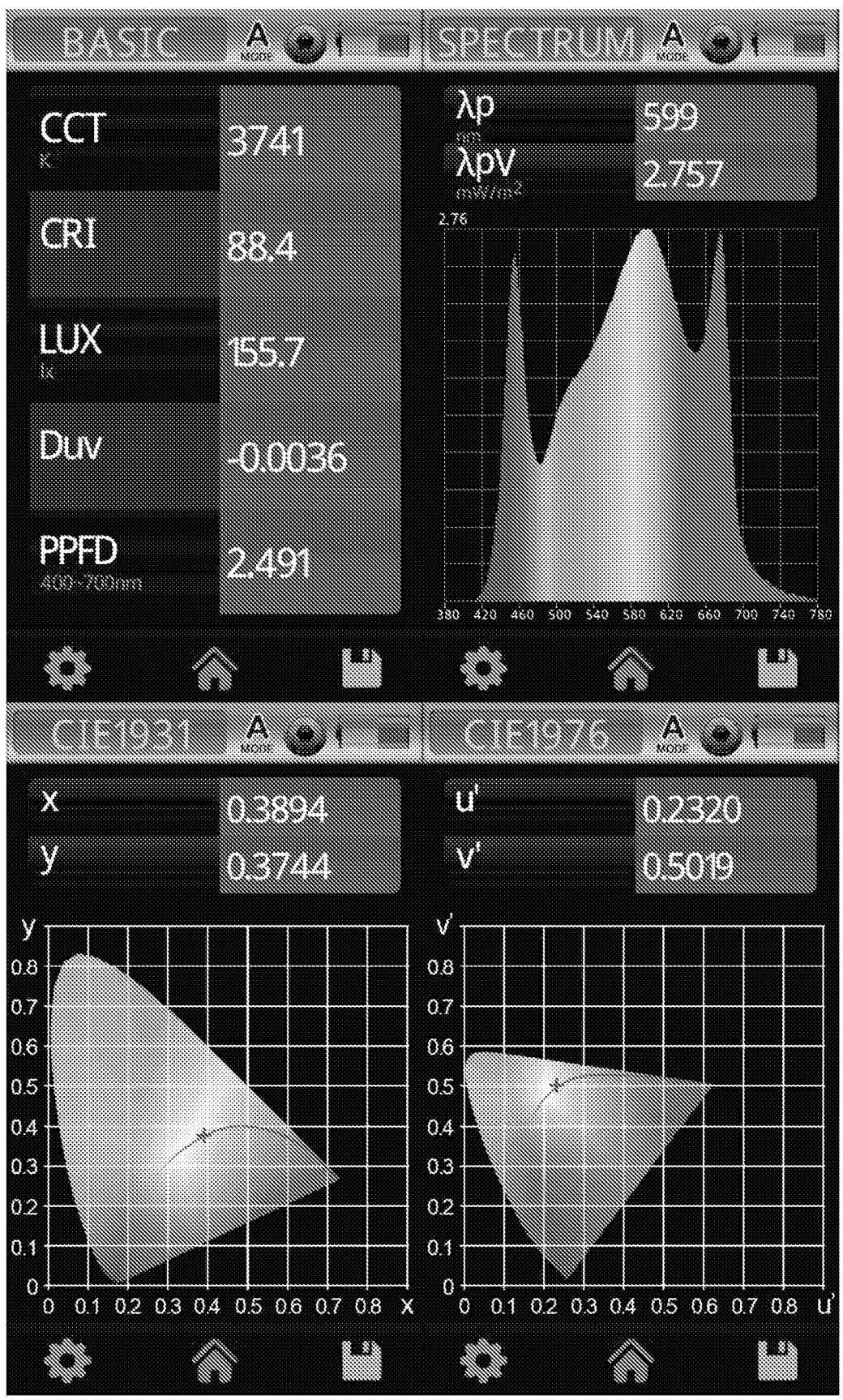
Fig. 1.2

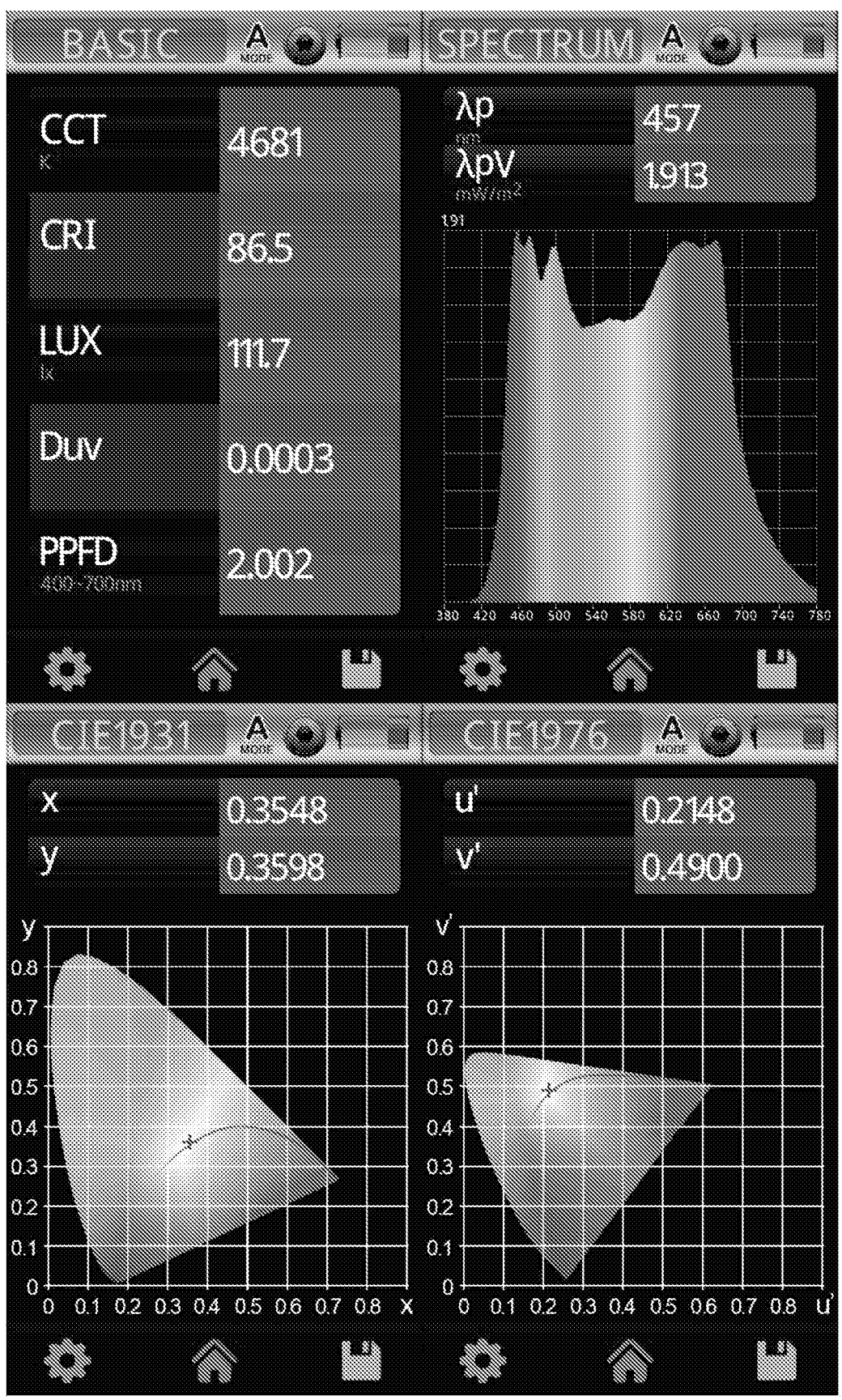
Fig. 1.3

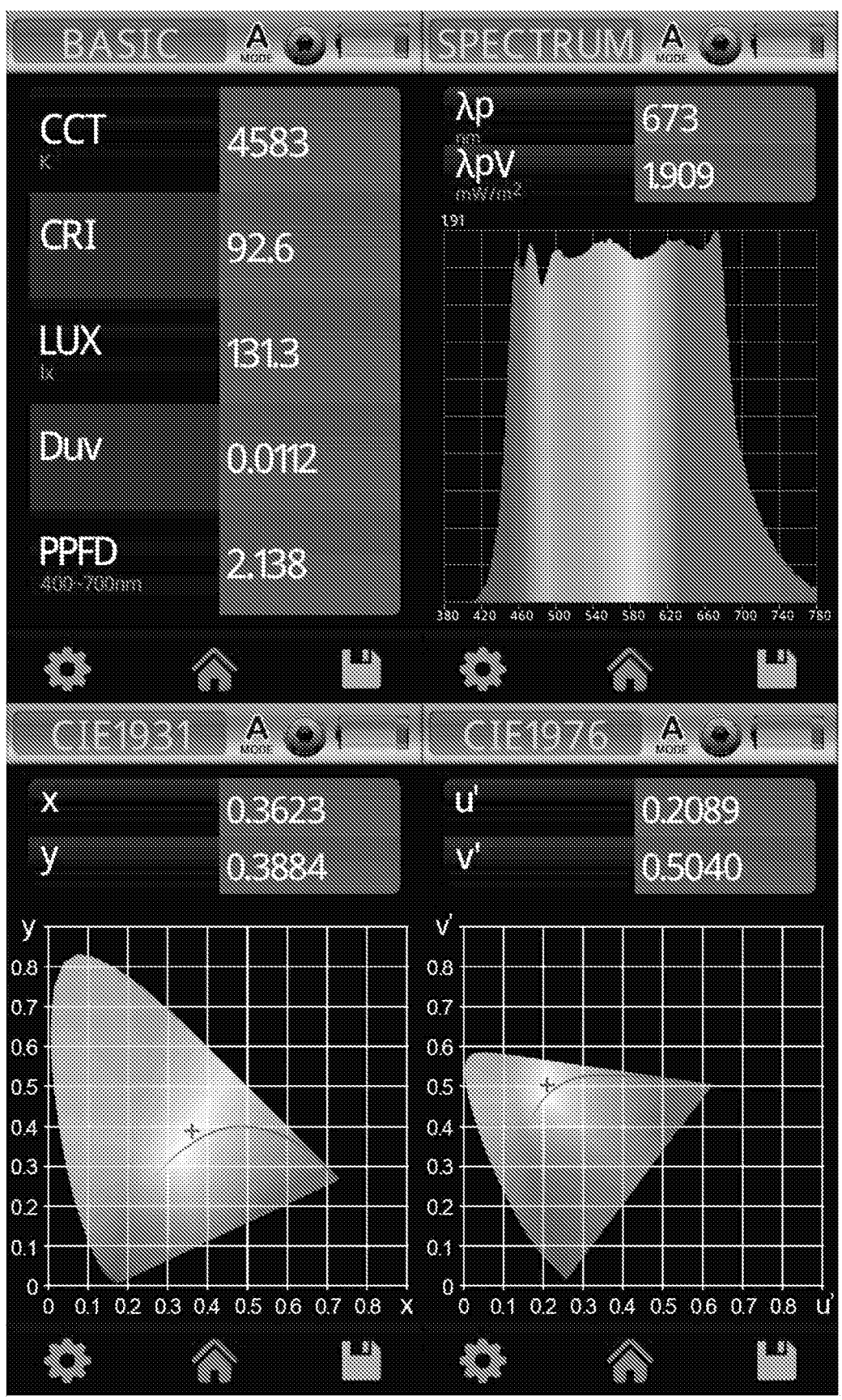
Fig. 1.4

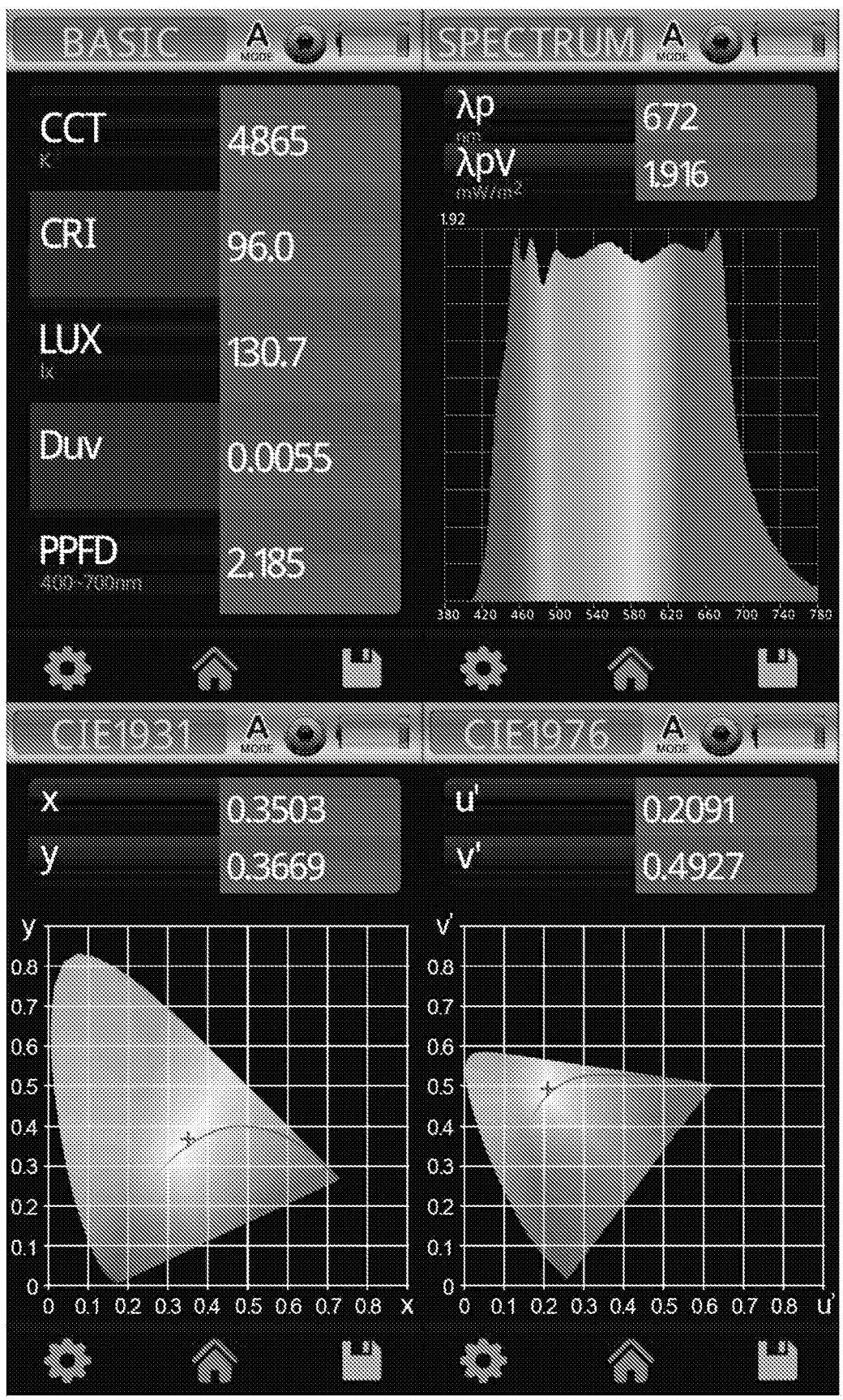
Fig. 1.5

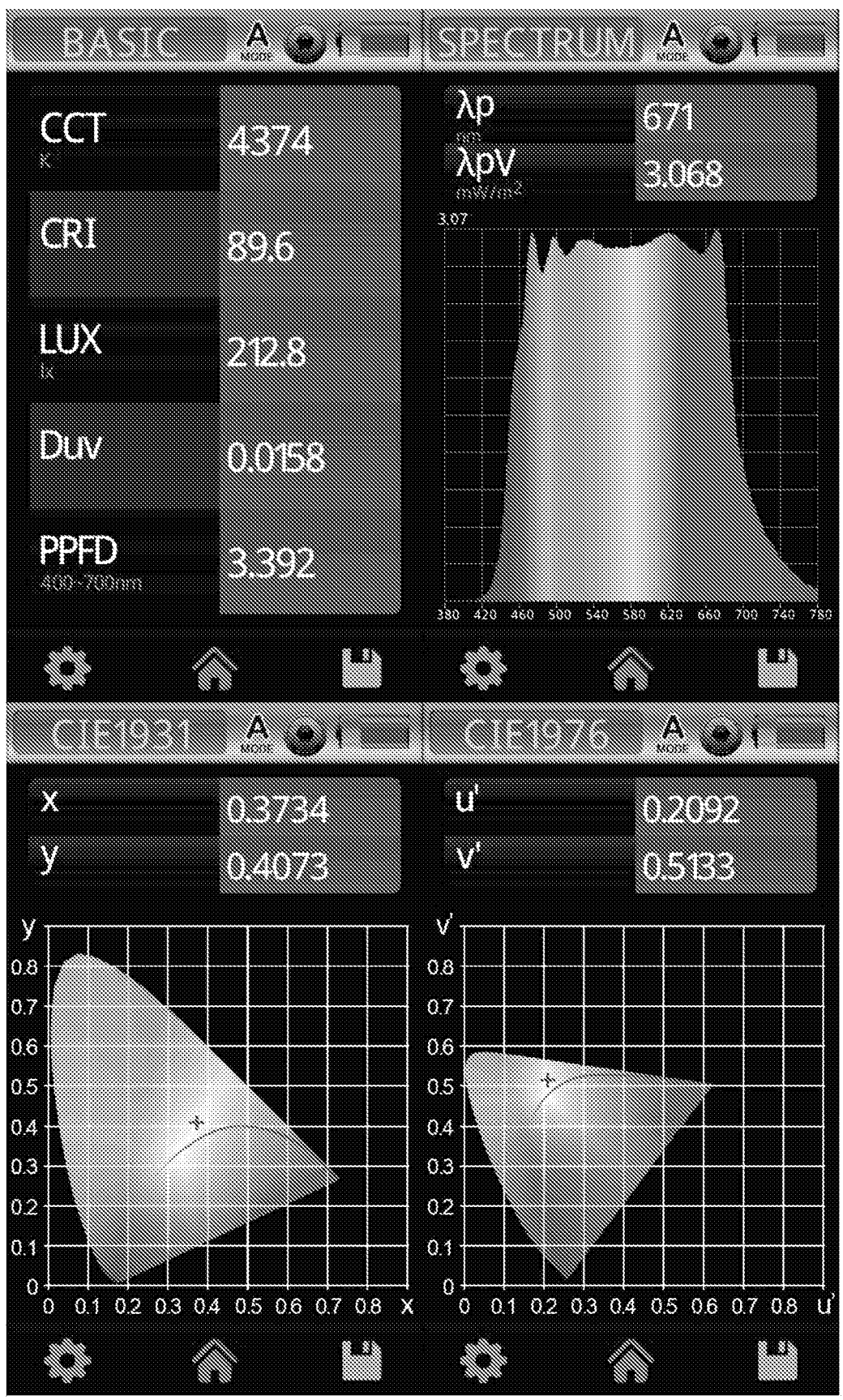
Fig. 1.6

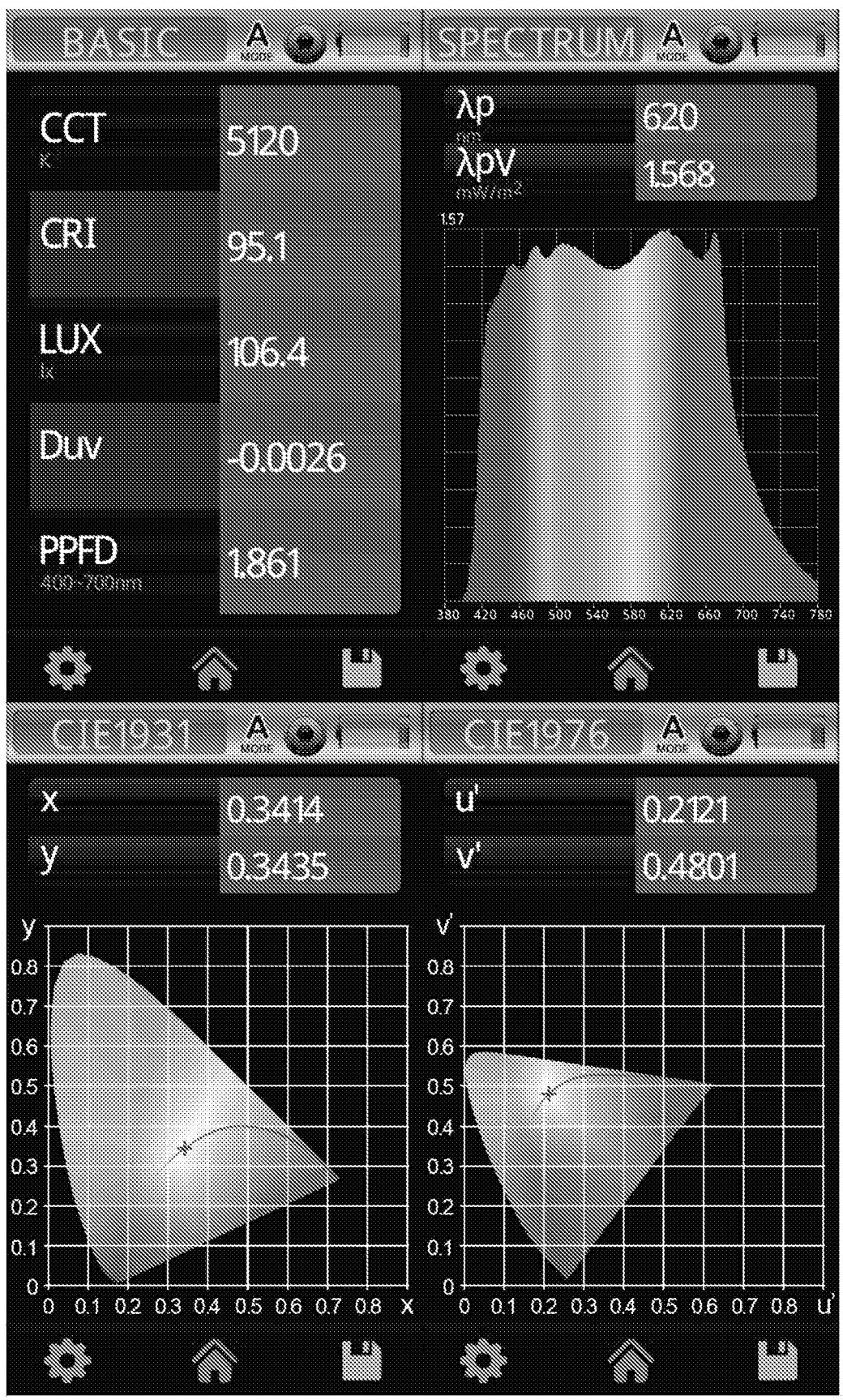
Fig. 1.7

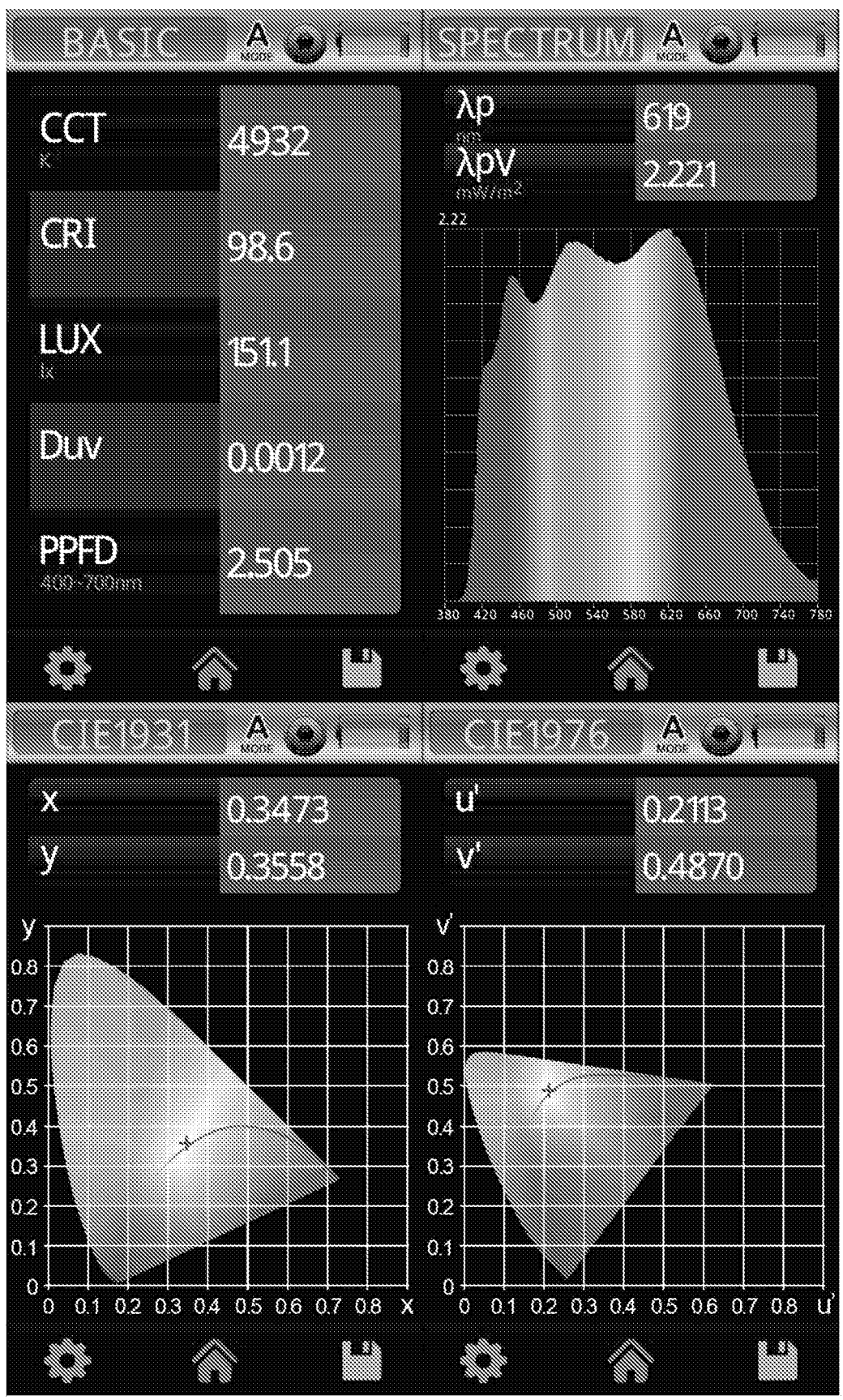
Fig. 1.8

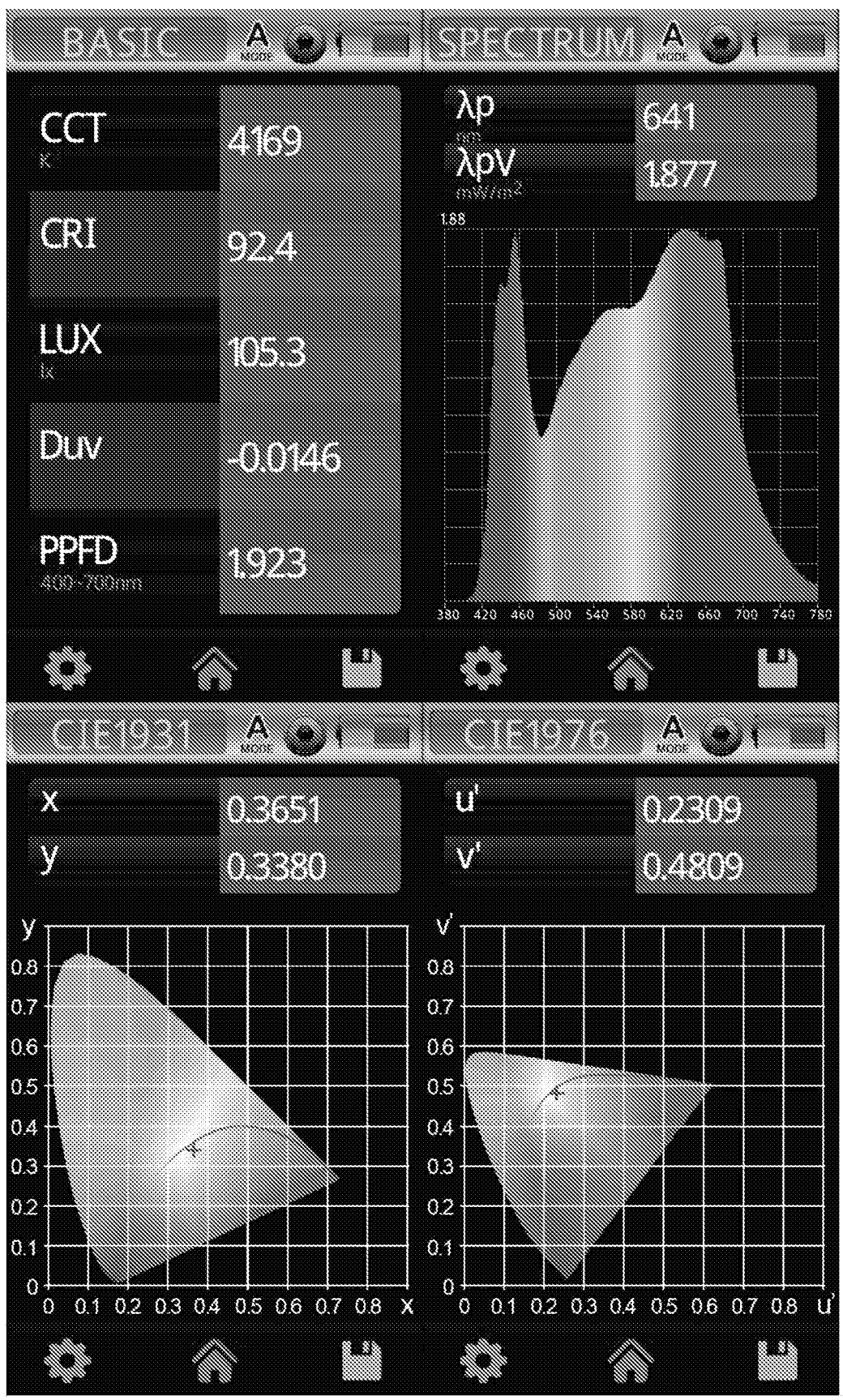
Fig. 1.9

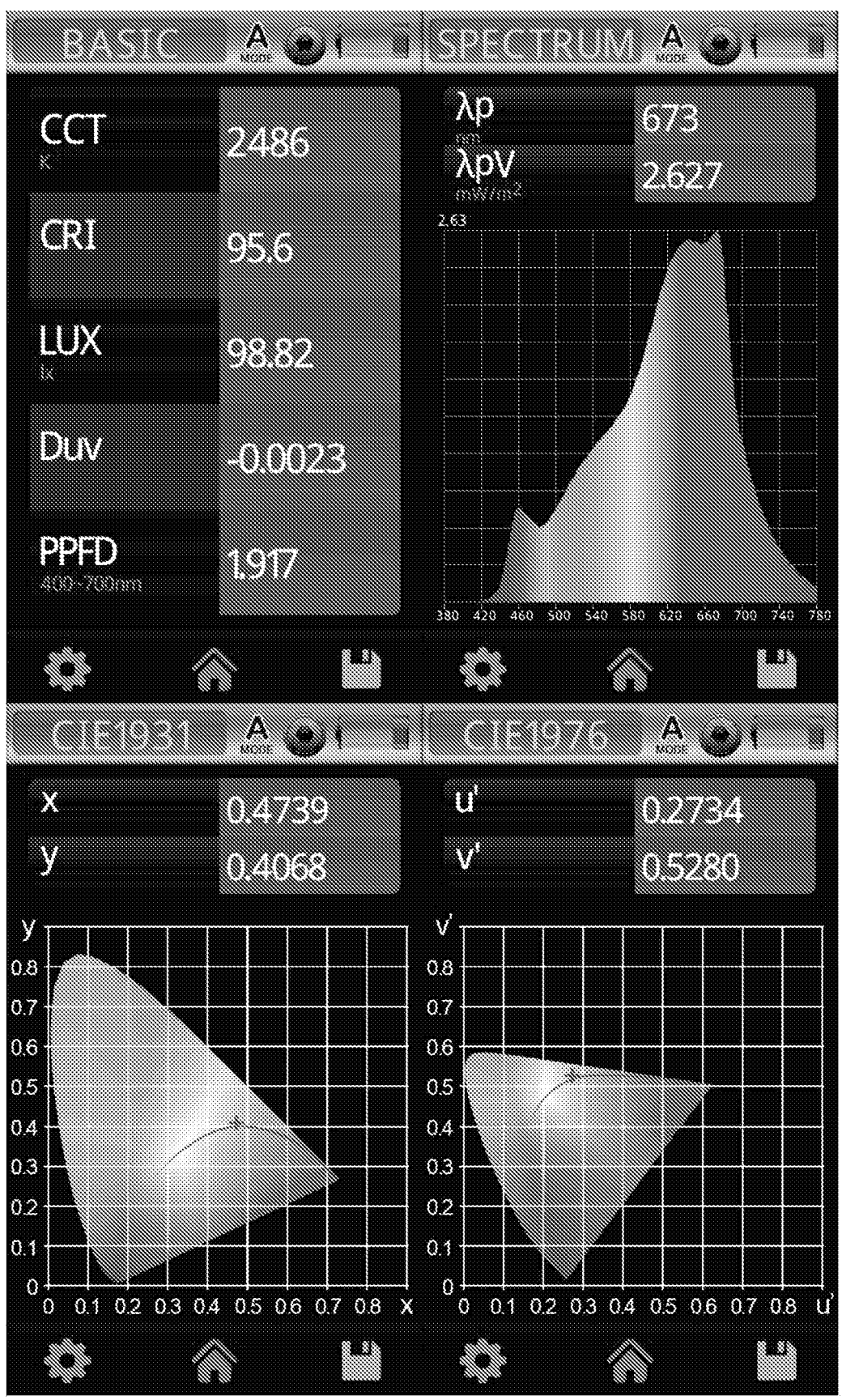
Fig. 1.10

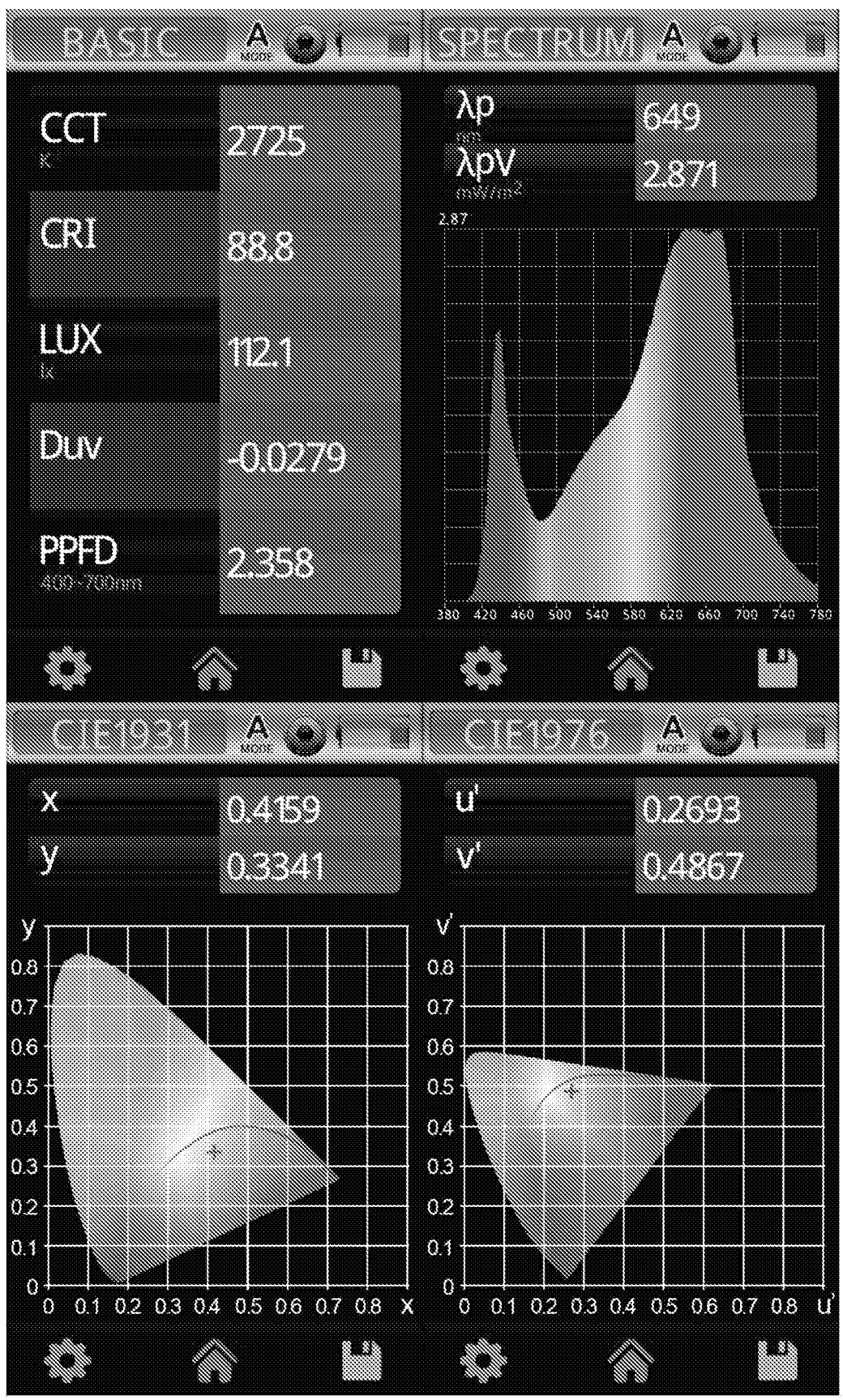
Fig. 1.11

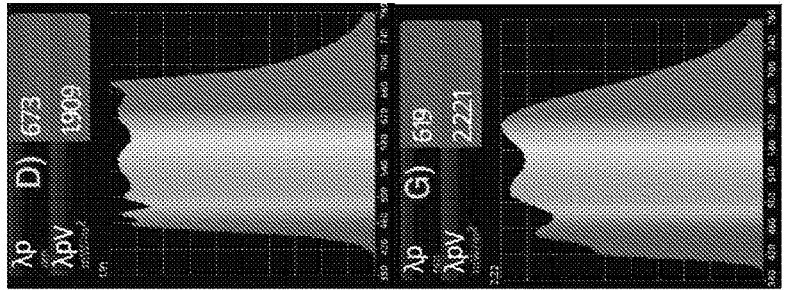
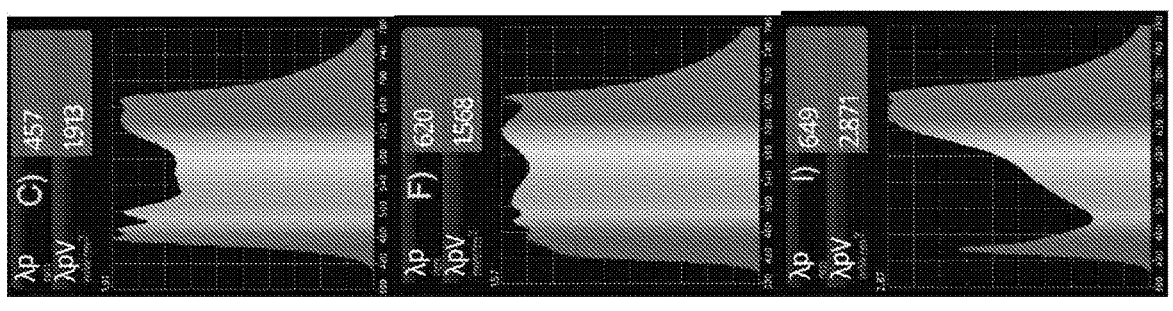
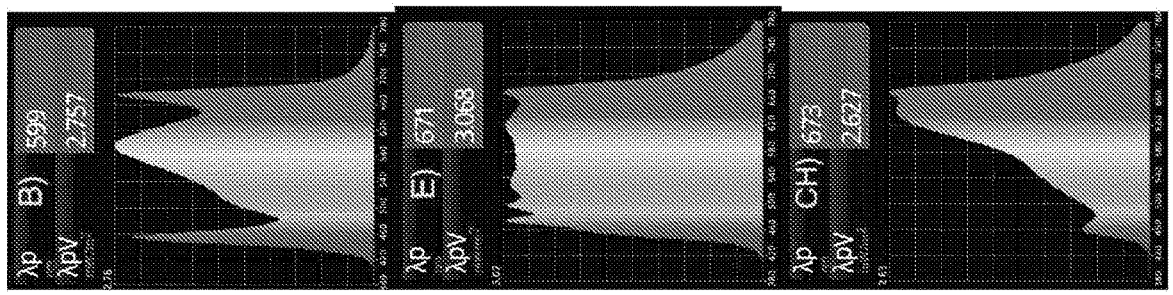
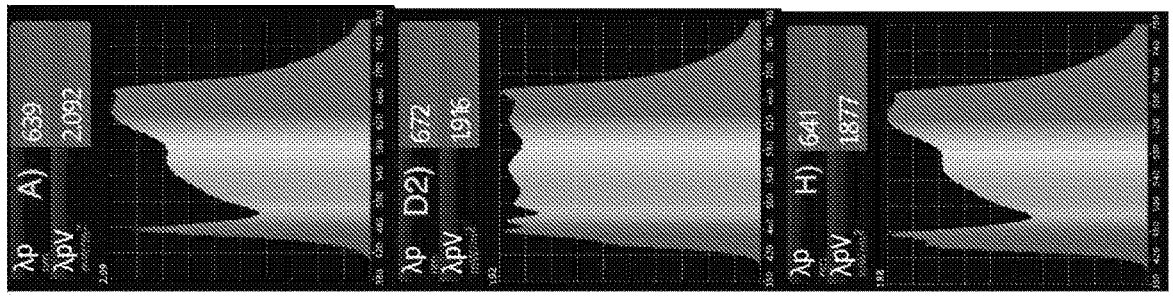
Fig. 2

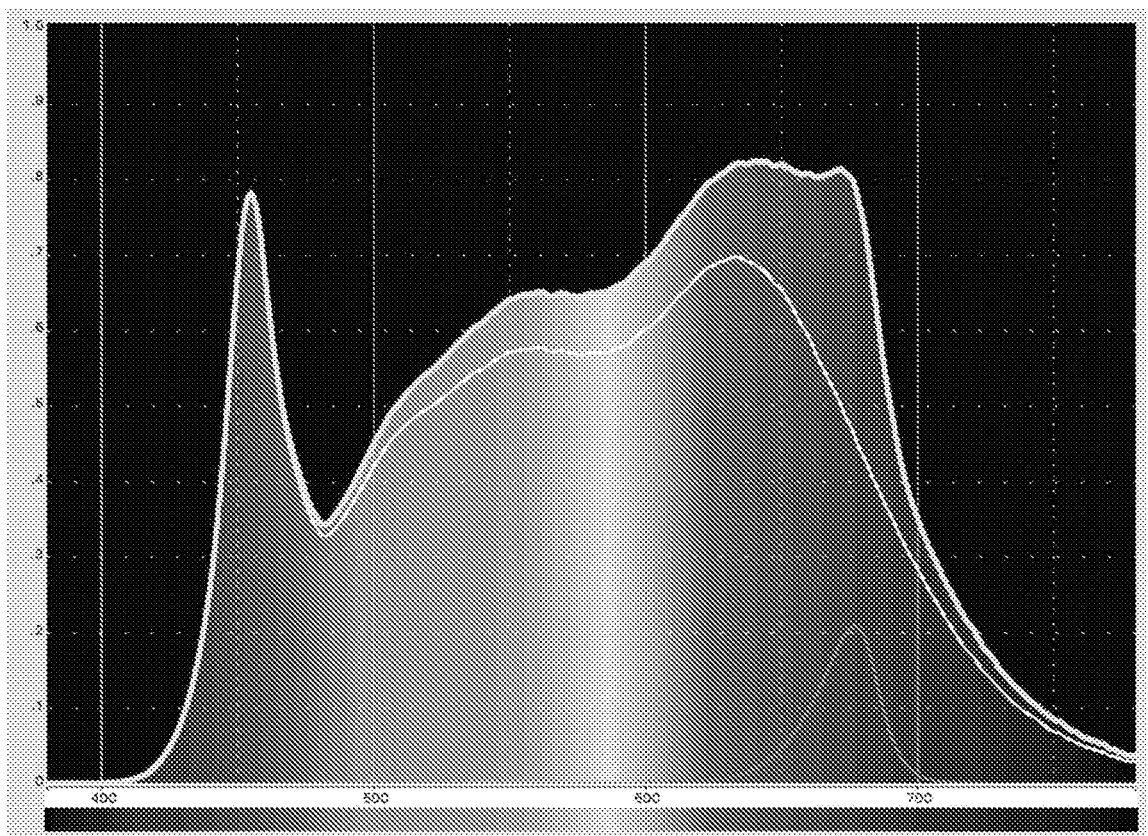
Fig. 3.1
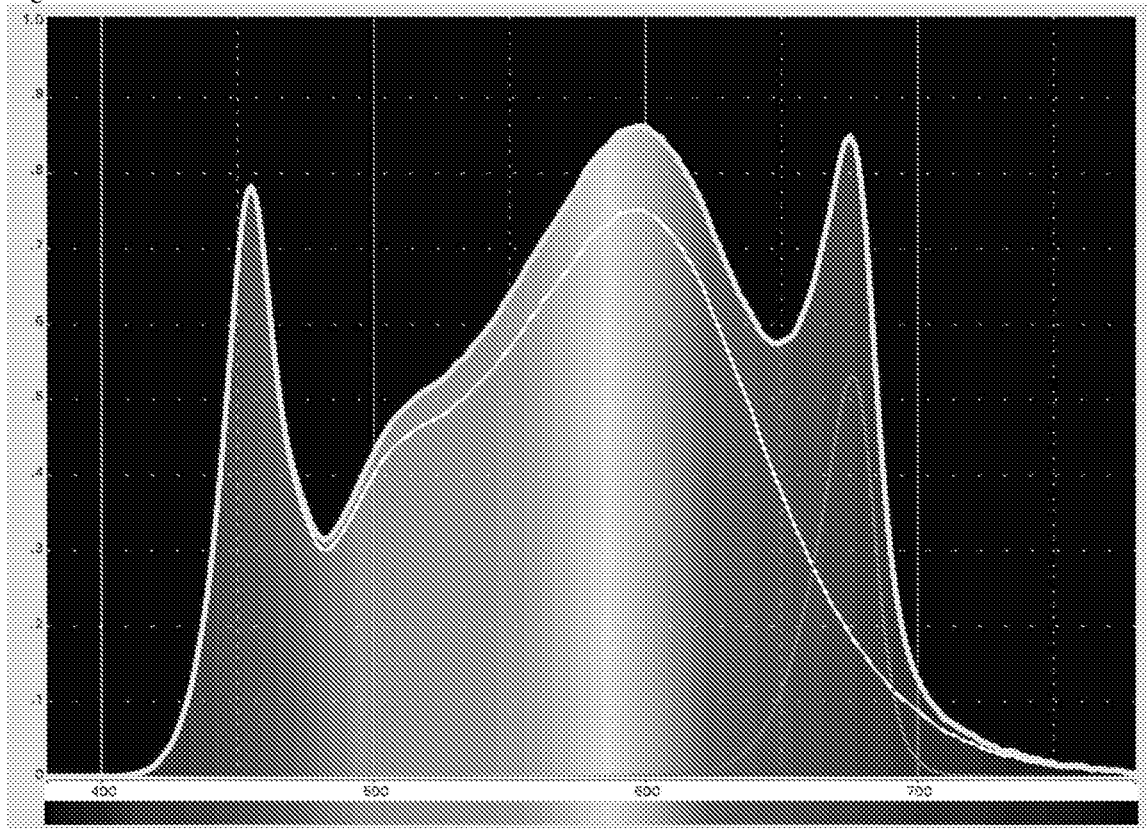
Fig. 3.2

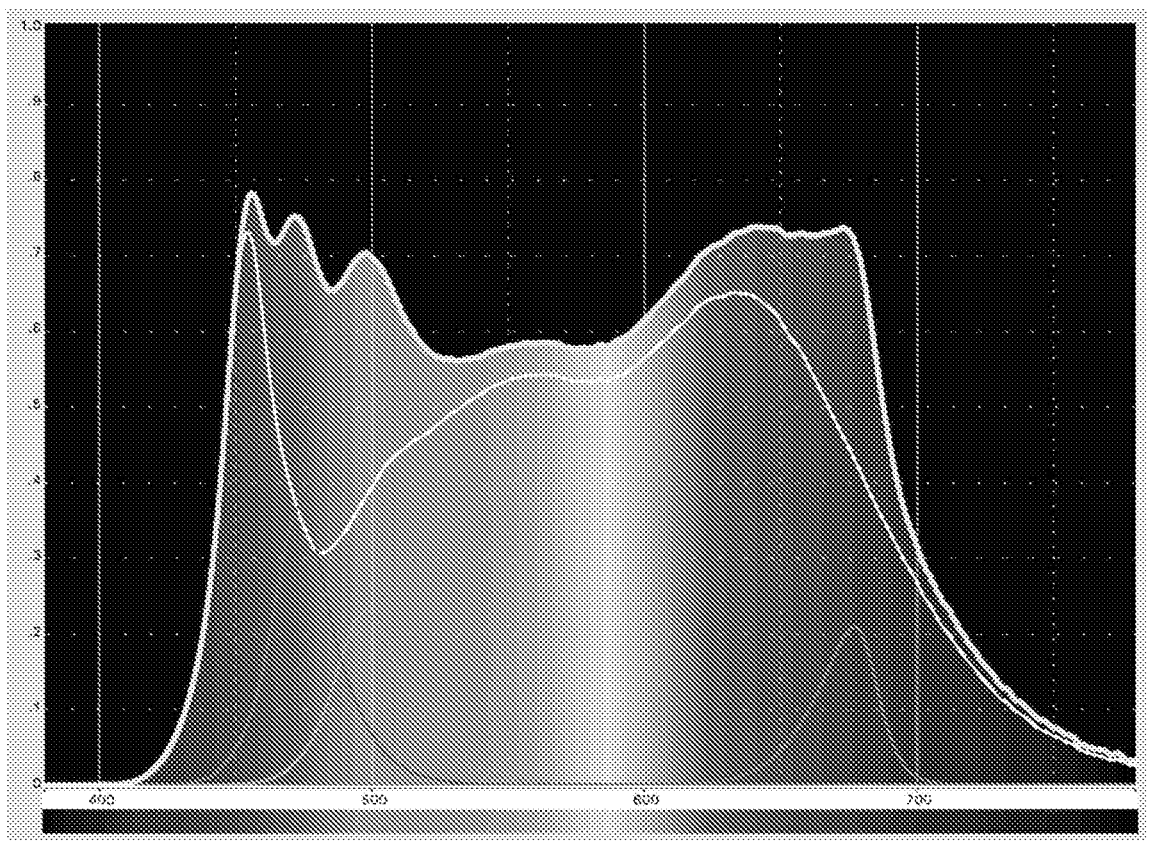
Fig. 3.3
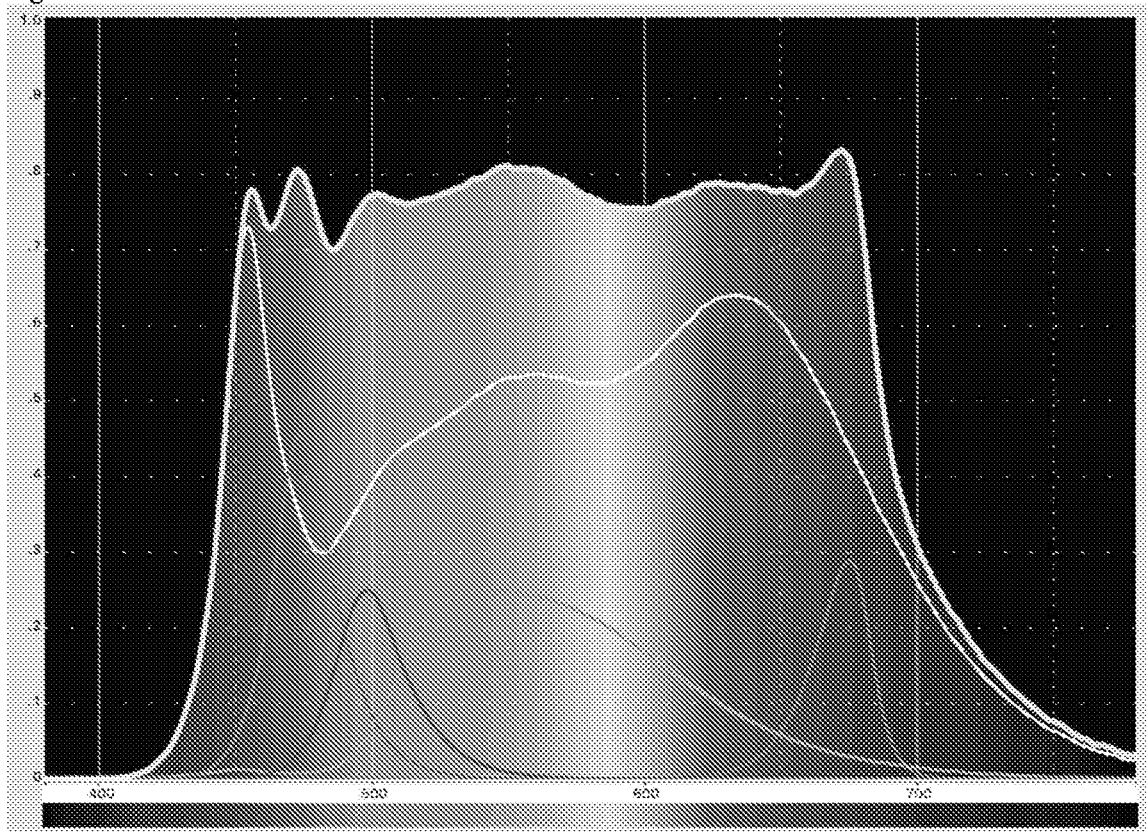
Fig. 3.4

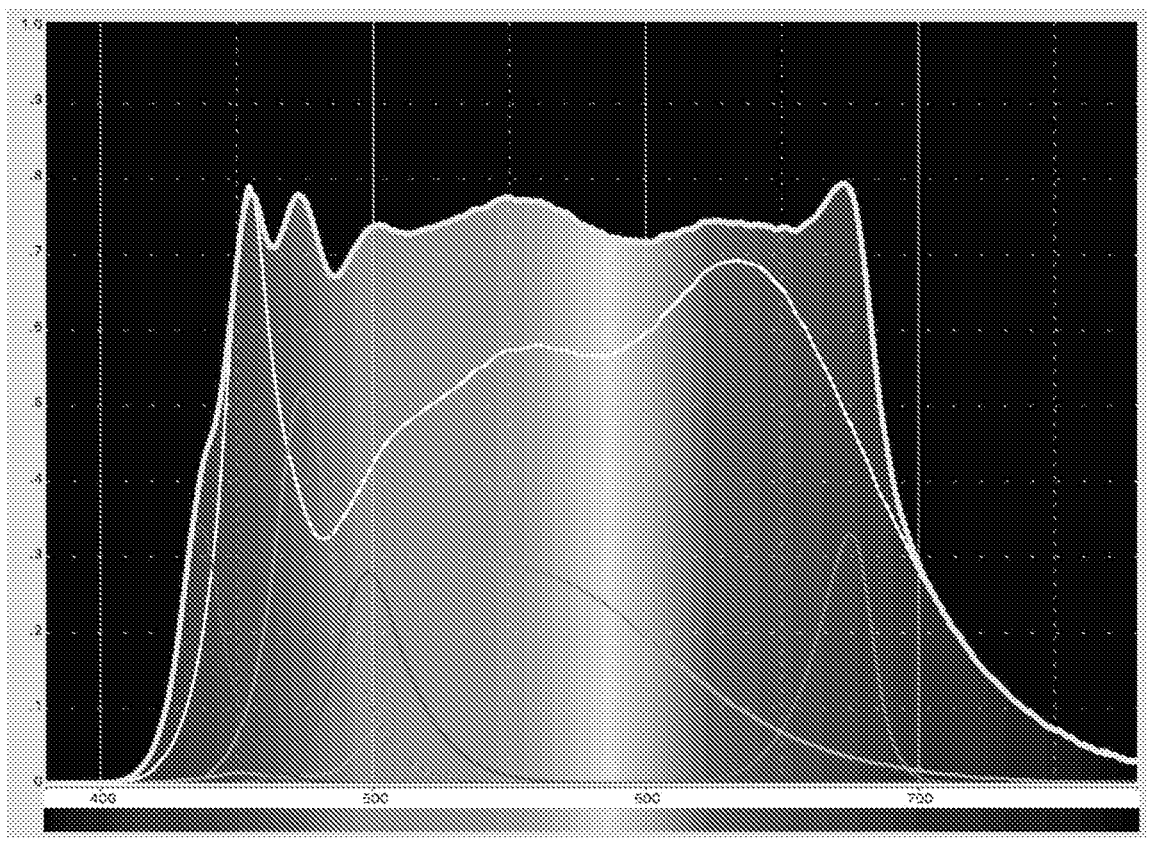
Fig. 3.5
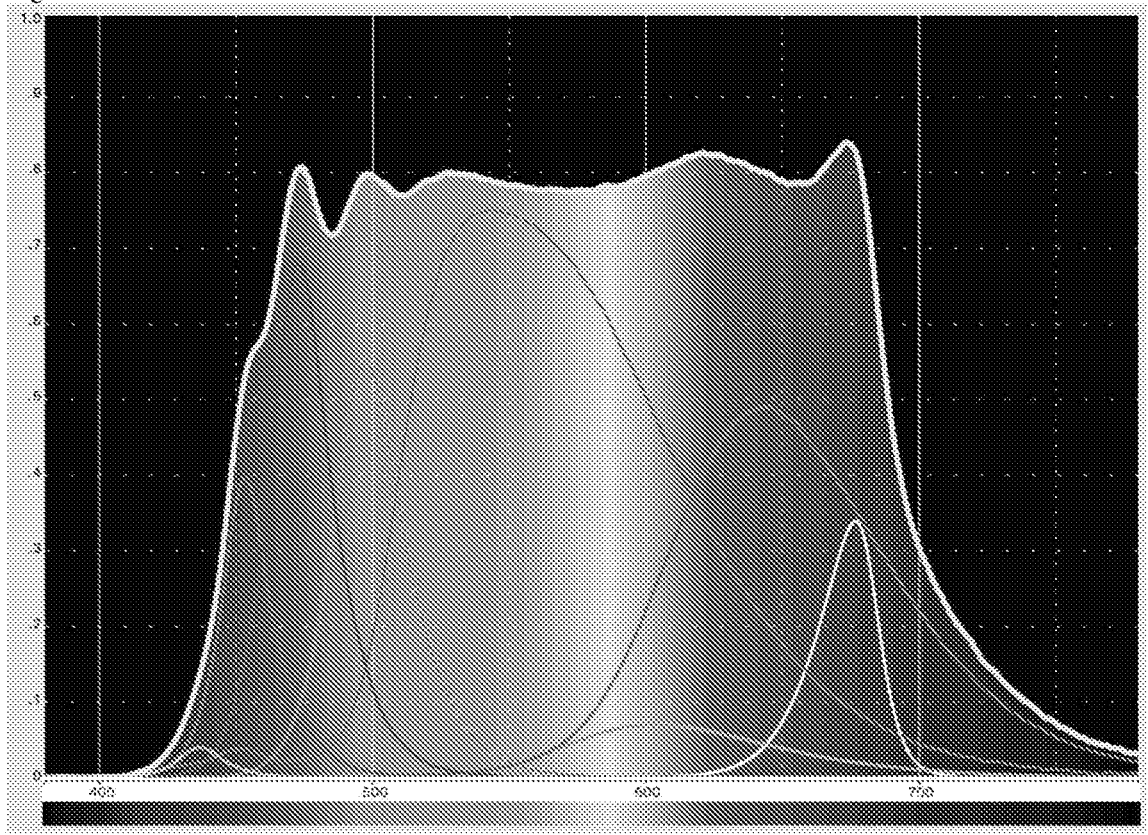
Fig. 3.6

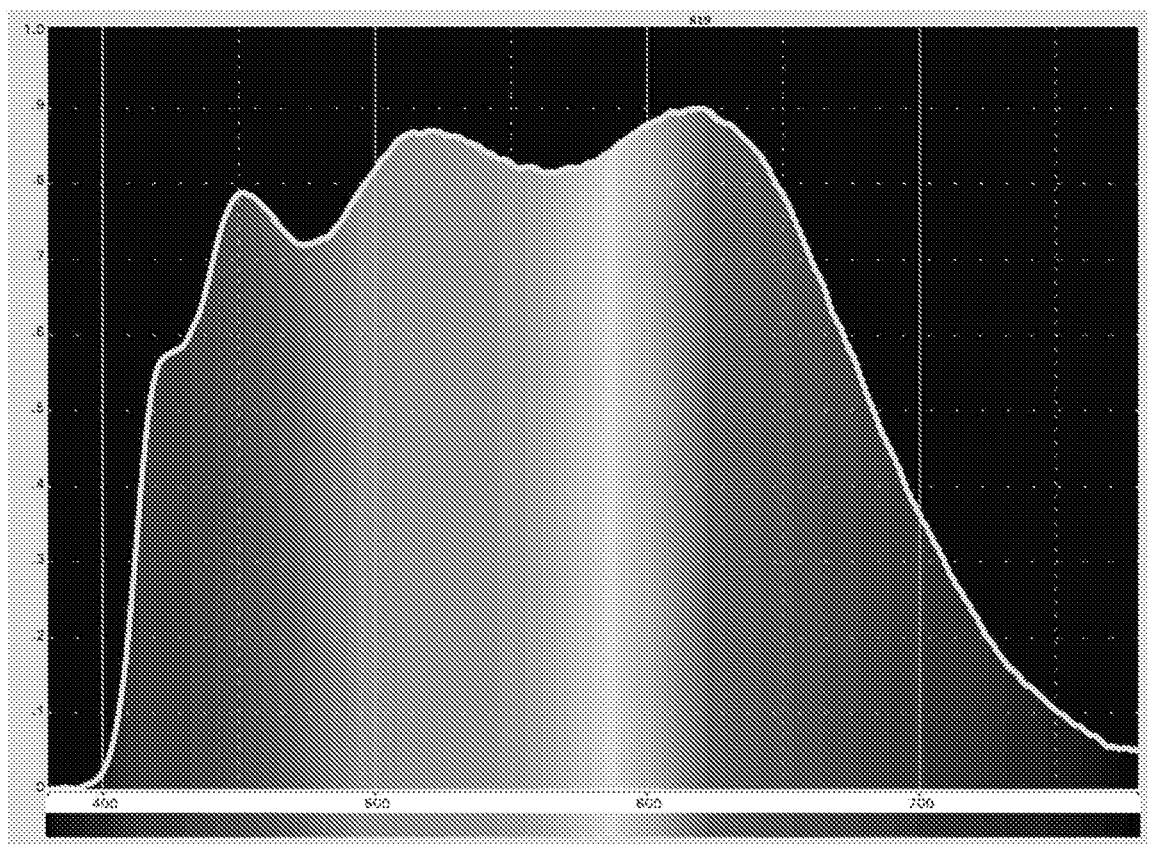
Fig. 3.7
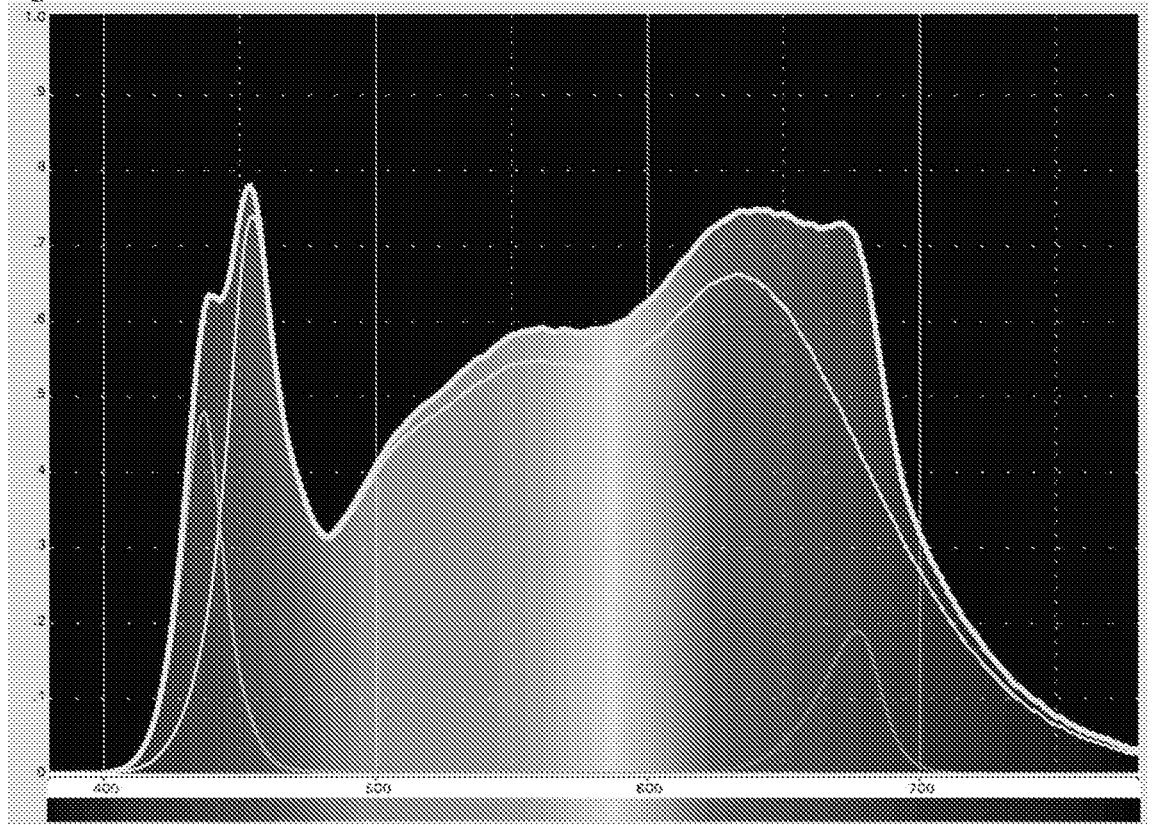
Fig. 3.8

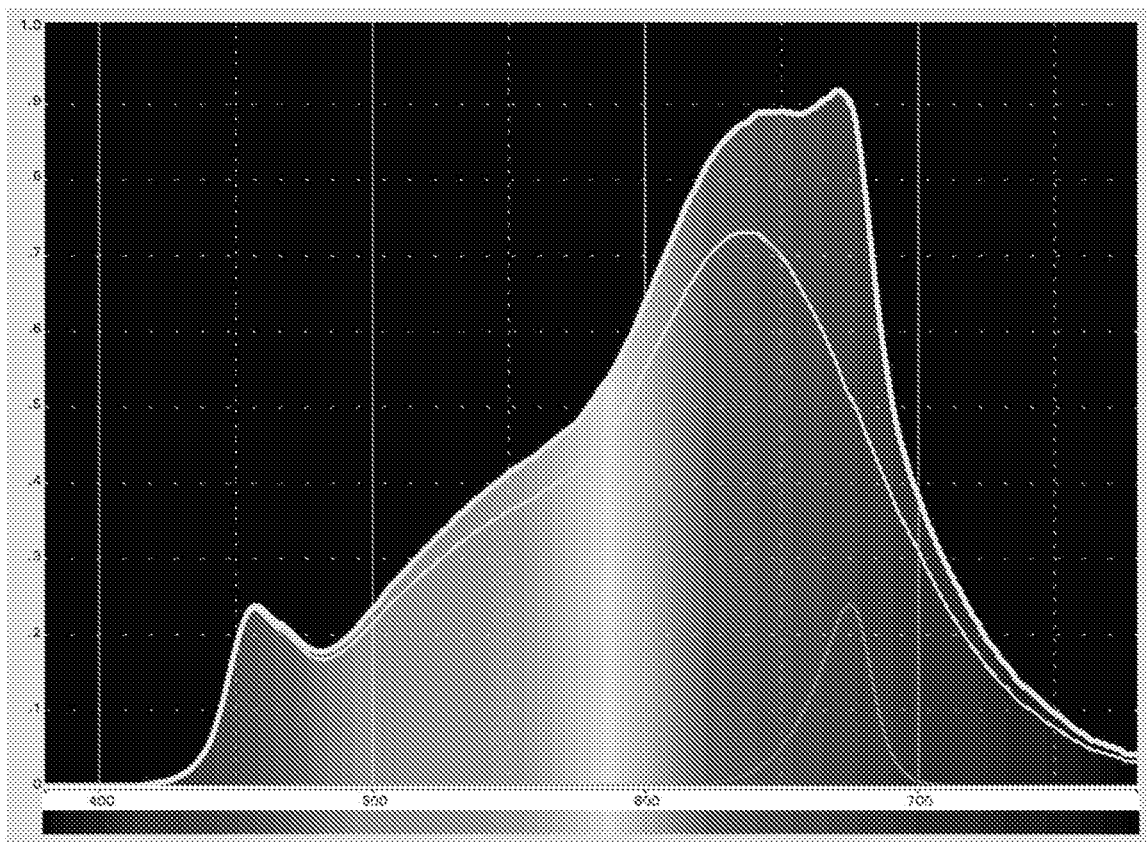
Fig. 3.9
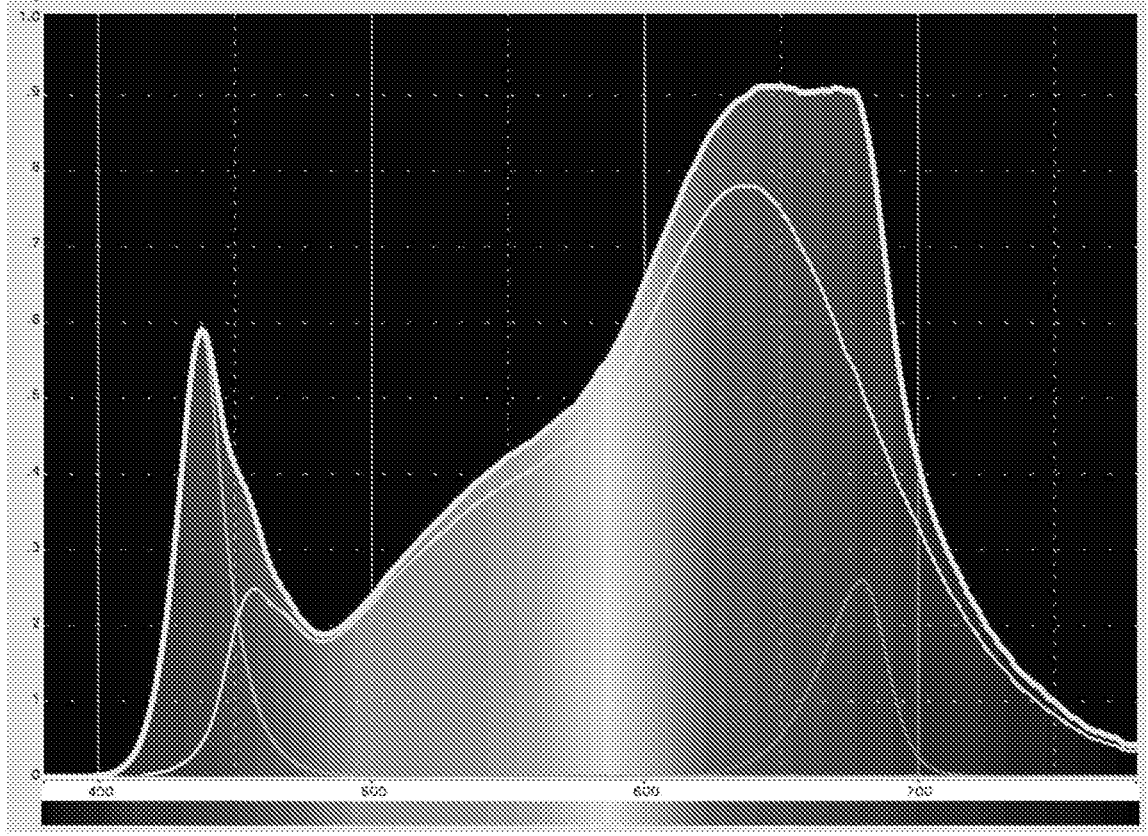
Fig. 3.10

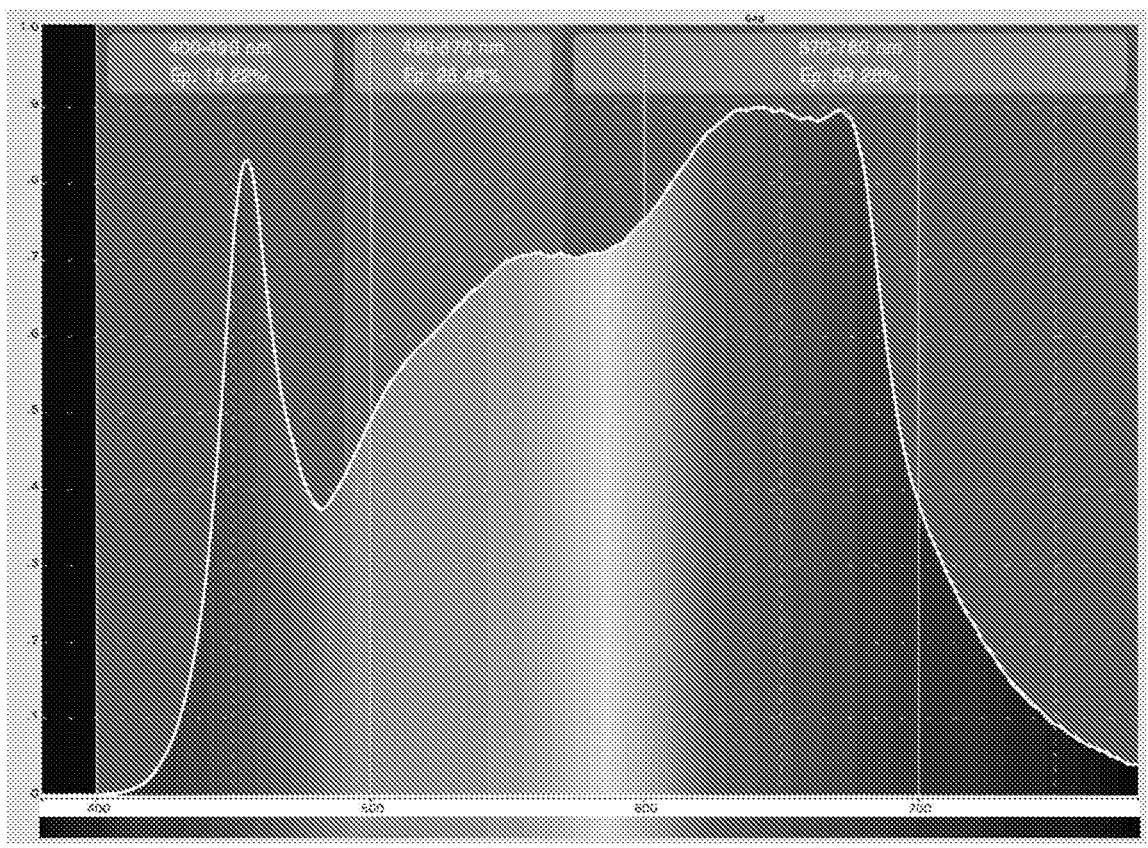
Fig. 4.1
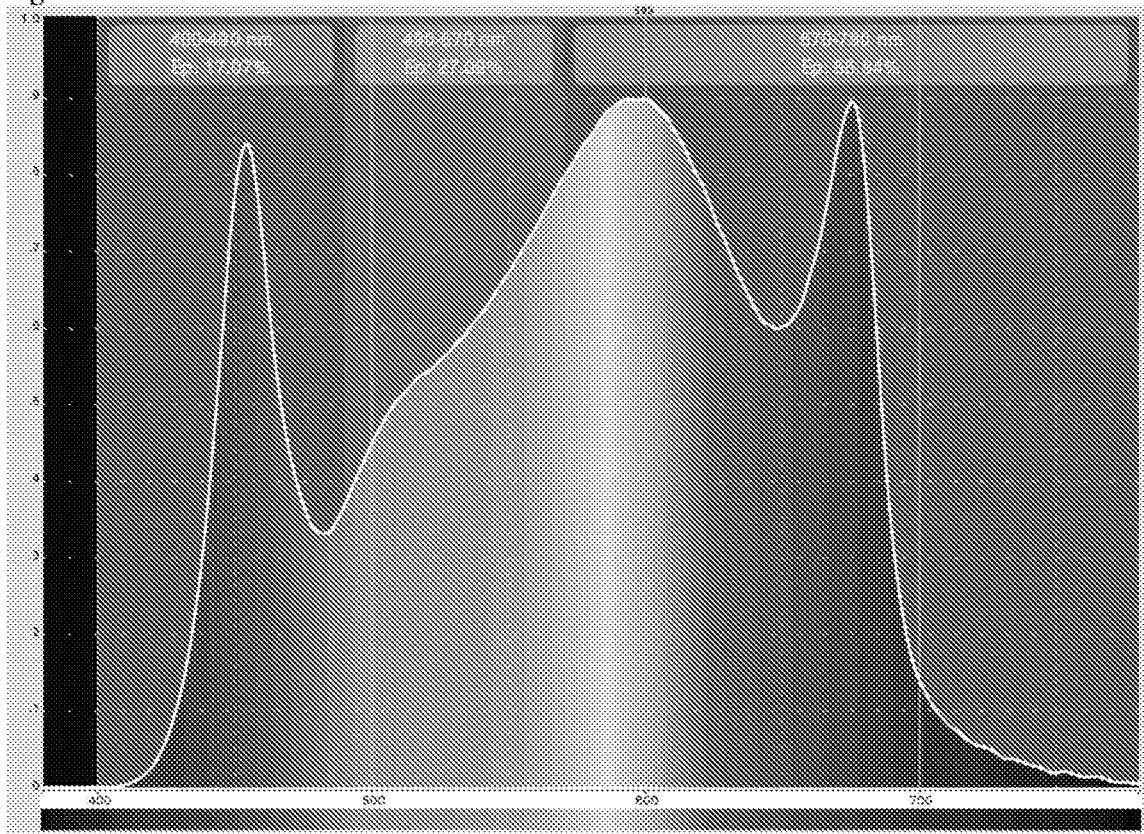
Fig. 4.2

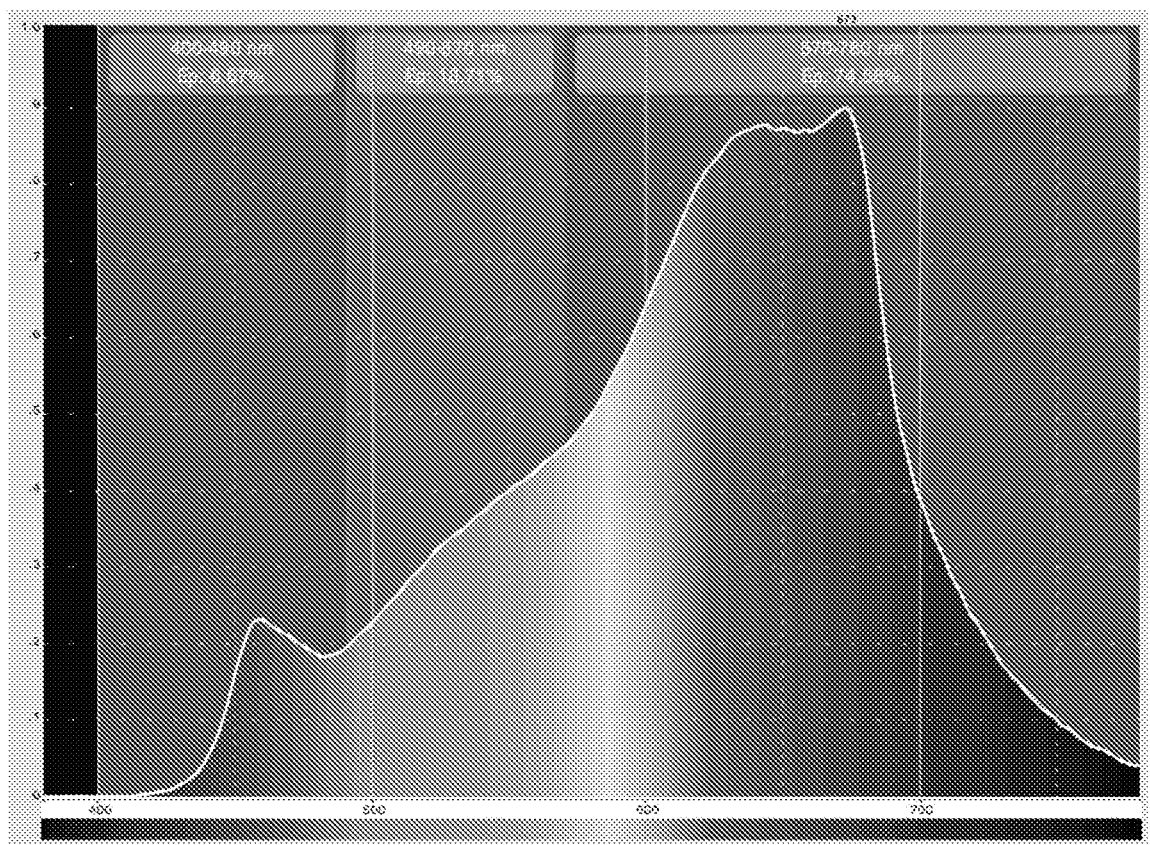
Fig. 4.3
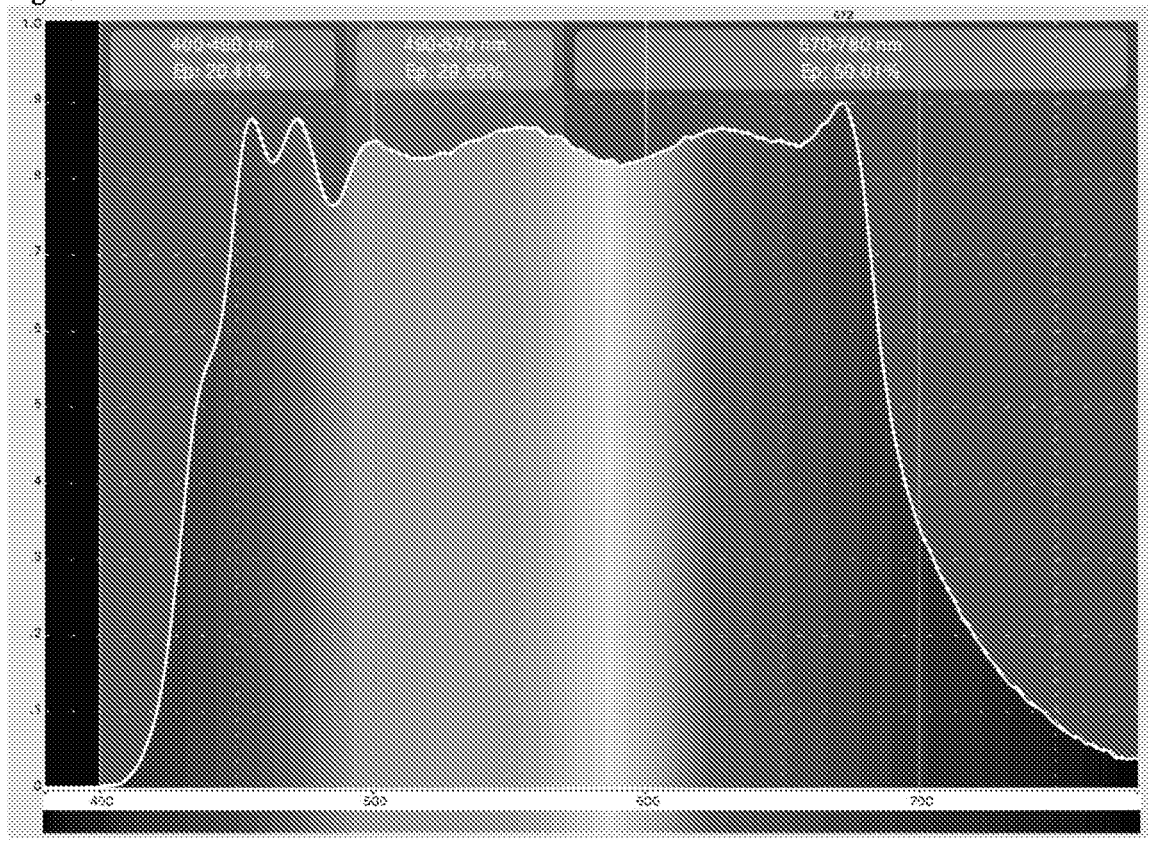
Fig. 4.4

| luminaire | used LED chips | current [mA] | decrease [V] | power consump-tion[mW] | CCT [K] | CRI | LUX [lx] | λp [nm] | λpV [mW/m²] | number of LED chips | total power consum. | total LUX [lx] | rel. power consum. [%] | ration LUX [%] |
|---|---|---|---|---|---|---|---|---|---|---|---|---|---|---|
| a) | 4000K CRI 98 | 120 | 3 | 360 | 4110 | 97,5 | 636,6 | 455 | 12,22 | 16 | 5760 | 10185,6 | 95,32 | 99,52 |
|  |  | 125 | 2,26 | 282,5 |  |  | 48,75 | 677 | 54,85 | 1 | 282,5 | 48,75 | 4,68 | 0,48 |
|  |  |  |  |  |  |  |  |  |  |  | 6042,5 | 10234,35 |  |  |
| b) | 4000K CRI 80 | 122 | 2,89 | 352,58 | 4021 | 85,2 | 886,4 | 455 | 16,27 | 16 | 5641,28 | 14182,4 | 89,61 | 99,16 |
|  |  | 100 | 2,18 | 218 |  |  | 40,17 | 676 | 45,45 | 3 | 654 | 120,51 | 10,39 | 0,84 |
|  |  |  |  |  |  |  |  |  |  |  | 6295,28 | 14302,91 |  |  |
| c) | 4000K CRI 98 | 122 | 3,01 | 367,22 | 4108 | 97,7 | 645,6 | 454 | 12,35 | 16 | 5875,52 | 10329,6 | 72,13 | 86,15 |
|  | 475 nm | 86 | 2,87 | 246,82 |  |  | 117 | 474 | 38,38 | 4 | 987,28 | 468 | 12,12 | 3,90 |
|  | 495 nm | 86 | 2,93 | 251,98 |  |  | 286 | 498 | 30,06 | 4 | 1007,92 | 1144 | 12,37 | 9,54 |
|  |  | 122 | 2,25 | 274,5 |  |  | 48,08 | 677 | 53,57 | 1 | 274,5 | 48,08 | 3,37 | 0,40 |
|  |  |  |  |  |  |  |  |  |  |  | 8145,22 | 11989,68 |  |  |
| d) | 4000K CRI 98 | 99 | 2,94 | 291,06 | 4116 | 97,6 | 546,4 | 455 | 10,64 | 16 | 4656,96 | 8742,4 | 69,29 | 70,28 |
|  | 475 nm | 72 | 2,83 | 203,76 |  |  | 106,4 | 474 | 34,48 | 2,5 | 509,4 | 266 | 7,58 | 2,14 |
|  | 495 nm | 72 | 2,87 | 206,64 |  |  | 251,9 | 498 | 26,66 | 2 | 413,28 | 503,8 | 6,15 | 4,05 |
|  |  | 72 | 2,09 | 150,48 |  |  | 30,13 | 675 | 34,12 | 2 | 300,96 | 60,26 | 4,48 | 0,48 |
|  | P.C. Lime | 99 | 2,83 | 280,17 |  |  | 955,5 | 543 | 17,45 | 3 | 840,51 | 2866,5 | 12,51 | 23,04 |
|  |  |  |  |  |  |  |  |  |  |  | 6721,11 | 12438,96 |  |  |
| d2) | 4000K CRI 98 | 99 | 2,94 | 291,06 | 4116 | 97,6 | 546,4 | 455 | 10,64 | 16 | 4656,96 | 8742,4 | 66,25 | 69,83 |
|  | 475 nm | 72 | 2,83 | 203,76 |  |  | 106,4 | 474 | 34,48 | 3 | 611,28 | 319,2 | 8,70 | 2,55 |
|  | 495 nm | 72 | 2,87 | 206,64 |  |  | 251,9 | 498 | 26,66 | 2 | 413,28 | 503,8 | 5,88 | 4,02 |
|  |  | 72 | 2,09 | 150,48 |  |  | 30,13 | 675 | 34,12 | 2 | 300,96 | 60,26 | 4,28 | 0,48 |
|  | P.C. Lime | 99 | 2,83 | 280,17 |  |  | 955,5 | 543 | 17,45 | 3 | 840,51 | 2866,5 | 11,96 | 22,90 |
|  |  | 72 | 2,86 | 205,92 |  |  | 27,44 | 437 | 67,91 | 1 | 205,92 | 27,44 | 2,93 | 0,22 |
|  |  |  |  |  |  |  |  |  |  |  | 7028,91 | 12519,6 |  |  |
| e) | P.C. Purple | 120 | 2,78 | 333,6 | 4218 | 47,7 | 297,8 | 644 | 19,49 | 8 | 2668,8 | 2382,4 | 24,38 | 12,63 |
|  | P.C. Lime | 120 | 2,87 | 344,4 |  |  | 1129 | 544 | 20,7 | 12 | 4132,8 | 13548 | 37,75 | 71,81 |
|  | P.C. Amber | 120 | 2,87 | 344,4 | 1791 | 54,1 | 742,1 | 604 | 22,24 | 1 | 344,4 | 742,1 | 3,15 | 3,93 |
|  |  | 120 | 2,98 | 357,6 |  |  | 152,4 | 473 | 49,79 | 4 | 1430,4 | 609,6 | 13,07 | 3,23 |
|  | 495 nm | 120 | 3,08 | 369,6 |  |  | 361 | 497 | 37,87 | 4 | 1478,4 | 1444 | 13,50 | 7,65 |
|  |  | 120 | 2,24 | 268,8 |  |  | 47,73 | 677 | 53,25 | 2 | 537,6 | 95,46 | 4,91 | 0,51 |
|  |  | 120 | 2,96 | 355,2 |  |  | 43,73 | 437 | 105,6 | 1 | 355,2 | 43,73 | 3,24 | 0,23 |
|  |  |  |  |  |  |  |  |  |  |  | 10947,6 | 18865,29 |  |  |

Fig. 5

| | | | | | | | | | | | | | |
|---|---|---|---|---|---|---|---|---|---|---|---|---|---|
| | Sunlike 5000K | 152 | 3,14 | 477,28 | 5141 | 96,8 | 716 | 622 | 10,52 | 16 | 7636,48 | 11456 | 96,92 | 98,76 |
| f) | 473 nm | 10 | 2,54 | 25,4 | | | 19,99 | 477 | 6,279 | 3 | 76,2 | 59,97 | 0,97 | 0,52 |
| | 495 nm | 10 | 2,45 | 24,5 | | | 47,34 | 501 | 4,584 | 1 | 24,5 | 47,34 | 0,31 | 0,41 |
| | 672 nm | 10 | 1,77 | 17,7 | | | 4,609 | 673 | 5,625 | 8 | 141,6 | 36,872 | 1,80 | 0,32 |
| | | | | | | | | | | | 7878,78 | 11600,18 | 100 | 100 |
| g) | Sunlike 5000K | 152 | 3,14 | 477,28 | 5141 | 96,8 | 716 | 622 | 10,52 | 16 | 7636,48 | 11456 | 100 | 99,10 |
| | 4000K CRI 98 | 120 | 3 | 360 | 4110 | 97,5 | 636,6 | 455 | 12,22 | 16 | 5760 | 10185,6 | 89,81 | 0,47 |
| h) | | 125 | 2,26 | 282,5 | | | 48,75 | 677 | 54,85 | 1 | 282,5 | 48,75 | 4,40 | 0,42 |
| | | 125 | 2,97 | 371,25 | | | 43,61 | 437 | 107 | 1 | 371,25 | 43,61 | 5,79 | |
| | | | | | | | | | | | 6413,75 | 10277,96 | | |
| ch) | 2700K CRI 98 | 120 | 3 | 360 | 2653 | 96,2 | 511,1 | 635 | 12,55 | 16 | 5760 | 8177,6 | 95,23 | 99,31 |
| | | 70 | 2,06 | 144,2 | | | 28,5 | 675 | 33,21 | 2 | 288,4 | 57 | 4,77 | 0,69 |
| | | | | | | | | | | | 6048,4 | 8234,6 | | |
| i) | 2700K CRI 98 | 120 | 3 | 360 | 2653 | 96,2 | 511,1 | 635 | 12,55 | 16 | 5760 | 8177,6 | 85,31 | 98,51 |
| | | 182 | 2,39 | 434,98 | | | 63,37 | 679 | 70,33 | 1 | 434,98 | 63,37 | 6,44 | 0,76 |
| | | 182 | 3,06 | 556,92 | | | 60,55 | 437 | 139,4 | 1 | 556,92 | 60,55 | 8,25 | 0,73 |
| | | | | | | | | | | | 6751,9 | 8301,52 | | |

Fig. 5 (continued)

| Prototype luminaire | description | version | CRI | CCT | Duv | measurement number | subjective light assessment | Overall assessment, designation |
|---|---|---|---|---|---|---|---|---|
| luminaire a) | White LED 4000 K, CRI 98 + red LED 672 nm | with opaque diffusor | 97,1 | 3797 | -0,003 | 195837 | pleasant white, very slight hint of pink | OK |
| luminaire b) | White LED 4000 K, CRI 80 + red LED 672 nm | with opaque diffusor | 88,4 | 3741 | -0,0036 | 200914 | pleasant white, no tints | OK |
| luminaire c) | Pro-cognitive: white LED 4000 K, CRI 98 + 475 nm (blue) + 495 nm (turquoise) + 672 nm (red) | with opaque diffusor | 86,5 | 4681 | 0,0003 | 202928 | white, with blue tint | NO blue tint |
| luminaire d) | Pro-cognitive: white LED 4000 K, CRI 98 + 475 nm (blue) + 495 nm (turquoise) + lime 555 nm + 672 nm (red) | with opaque diffusor | 92,6 | 4583 | 0,0112 | 205842 | white, with green tint | NO green tint |
| luminaire d2) | Pro-cognitive: white LED 4000 K, CRI 98 + 475 nm (blue) + 495 nm (turquoise) + lime 555 nm + 672 nm (red) + 440 nm blue | with opaque diffusor | 96 | 4855 | 0,0055 | 210803 | white, no tints | OK (vs. version d, contains additionally 440nm) |
| luminaire e) | Purple (450 nm) with luminophore at 640 nm + 475 nm +495 nm + PC lime 555 nm + PC amber 600 nm + 672 nm + 440 nm blue | with opaque diffusor | 89,6 | 4374 | 0,0158 | 193905 | distinctly greenish tint without 440 nm | NO, artificial unnatural green light |
| luminaire f) | Sunlike 5000K + 475 nm + 495 nm + 672 nm | with opaque diffusor | 95,1 | 5120 | 0,0026 | 213437 | white, looks artificial | NO, the light appears gray + caution - BL hazard 420nm |
| luminaire g) | Sunlike 5000K | with opaque diffusor | 98,6 | 4932 | 0,0012 | 213917 | cold white | very cold, also caution - BL hazard 420 nm |
| luminaire h) | White LED 4000 K, CRI 98 + red LED 672 nm + 440nm (blue) | with opaque diffusor | 92,4 | 4169 | -0,0146 | 191334 | white, with blue tint | OK |
| luminaire ch) | White LED 2700 K, CRI 98 + red LED 672 nm | with opaque diffusor | 95,6 | 2486 | -0,0023 | 194930 | warm white | ok, relaxing |
| luminaire i) | White LED 2700 K, CRI 98 + red LED 672 nm + 440nm (blue) | with opaque diffusor | 88,8 | 2725 | -0,0279 | 193457 | warm white with violet tint | NO, unnatural |

Fig. 6

7A

| % | spectral component | | | |
|---|---|---|---|---|
| spectrum | Blue | green | red | total |
| A | 15,22 | 25,48 | 59,28 | 99,98 |
| B | 17,07 | 27,09 | 55,84 | 100 |
| H | 20,46 | 23,83 | 55,69 | 99,98 |
| CH | 6,67 | 18,71 | 74,58 | 99,96 |
| D2 | 20,41 | 29,55 | 50,01 | 99,97 |

7B

| ratio | spectral component | | | |
|---|---|---|---|---|
| spectrum | Blue | green | red | total |
| A | 1,0 | 1,7 | 3,9 | 6,6 |
| B | 1,0 | 1,6 | 3,3 | 5,9 |
| H | 1,0 | 1,2 | 2,7 | 4,9 |
| CH | 1,0 | 2,8 | 11,2 | 15,0 |
| D2 | 1,0 | 1,4 | 2,5 | 4,9 |

7C

| | spectral component | | | |
|---|---|---|---|---|
| spektrum | Blue | green | red | total |
| A | 0,6 | 1,0 | 2,3 | 3,9 |
| B | 0,6 | 1,0 | 2,1 | 3,7 |
| H | 0,9 | 1,0 | 2,3 | 4,2 |
| CH | 0,4 | 1,0 | 4,0 | 5,3 |
| D2 | 0,7 | 1,0 | 1,7 | 3,4 |

7D

| % | spectral component | | |
|---|---|---|---|
| spectrum | Blue + green | red | total |
| A | 40,7 | 59,3 | 100,0 |
| B | 44,2 | 55,8 | 100,0 |
| H | 44,3 | 55,7 | 100,0 |
| CH | 25,4 | 74,6 | 100,0 |
| D2 | 50,0 | 50,0 | 100,0 |

7E

| ratio | spectral component | | |
|---|---|---|---|
| spectrum | Blue + green | red | total |
| A | 1,0 | 1,5 | 2,5 |
| B | 1,0 | 1,3 | 2,3 |
| H | 1,0 | 1,3 | 2,3 |
| CH | 1,0 | 2,9 | 3,9 |
| D2 | 1,0 | 1,0 | 2,0 |

Fig. 7

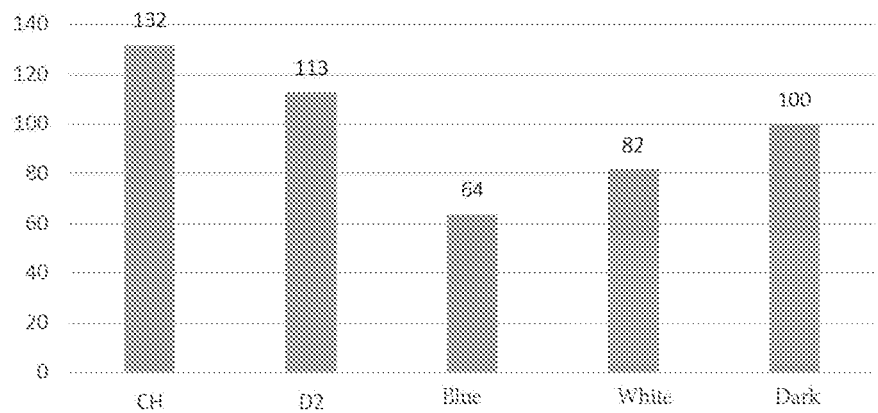
Fig. 8
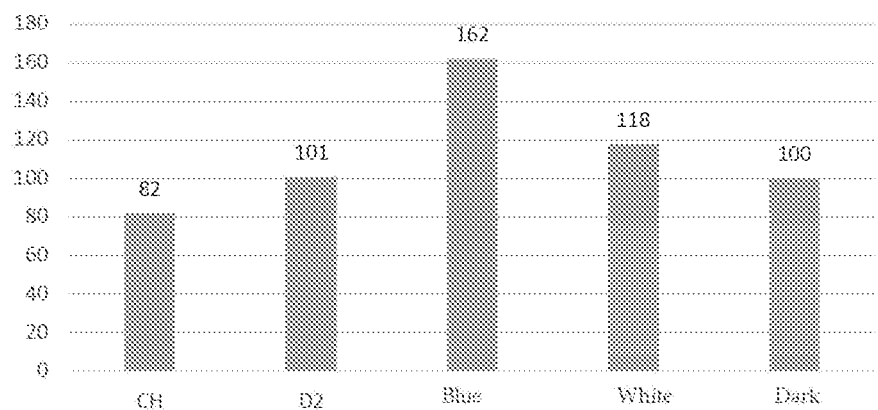
Fig. 9.1
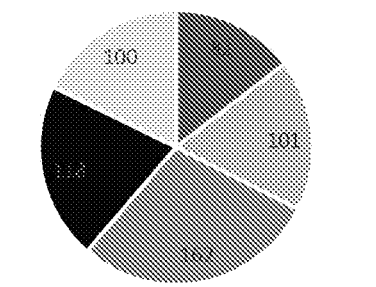
Fig. 9.2

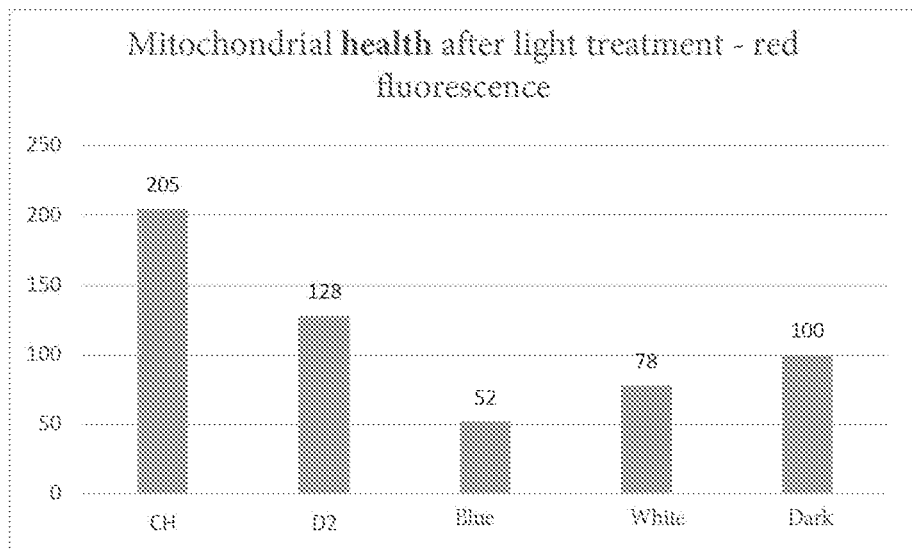
Fig. 9.3
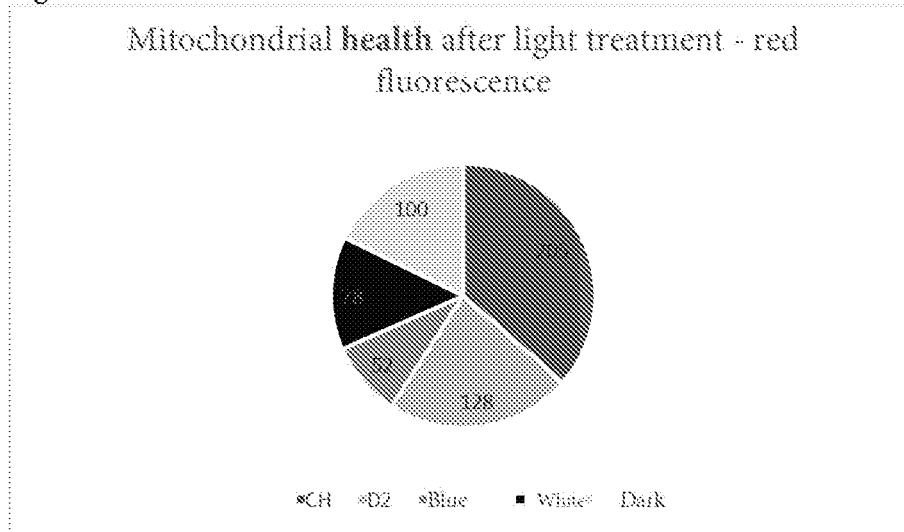
Fig. 9.4
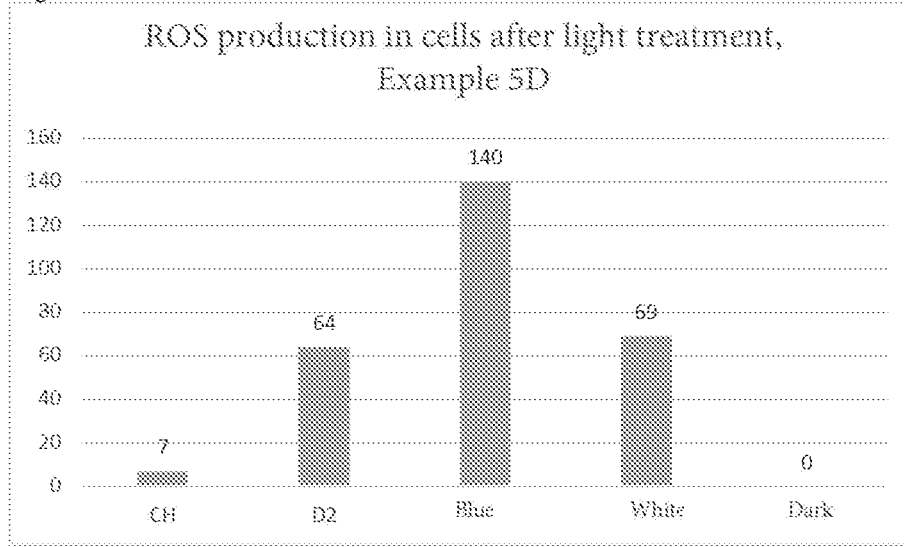
Fig. 10

| in vitro experiments on tissue cultures R28 | | energy mW/m² | | | energies sum | standardization to 100% | |
|---|---|---|---|---|---|---|---|
| | | blue spectral component | | red spectral component | | energy % | |
| | | | | | | blue spectral component | red spectral component |
| maximum search area | max | 400-490nm | | 570-780nm | | 400-490nm | 570-780nm |
| blue LED chip 440 nm | 437nm | 23.51634 | | 0.127254 | 23.643639 | 99.46% | 0.54% |
| White LED chip 4000 K, CRI | 455nm | 10.636298 | | 9.317944 | 19.954242 | 53.30% | 46.70% |
| luminaire D2 | 456nm | 1.872685 | | 1.916482 | 3.789167 | 49.42% | 50.58% |
| luminaire CH | 459nm | 0.674629 | | 2.626985 | 3.301614 | 20.43% | 79.57% |

Fig. 11

| Time (min) | Light emitter | | | |
|---|---|---|---|---|
| | Blue (number of living cells) | White (number of living cells) | Day white D2 (number of living cells) | Warm white CH (number of living cells) |
| 0 | 575 000 | 519 000 | 560 000 | 579 000 |
| 30 | 144 000 | 512 000 | 142 000 | 133 000 |
| 60 | 185 000 | 554 000 | 393 000 | 582 000 |
| 90 | 104 000 | 474 000 | 341 000 | 1 330 000 |
| 120 | 118 000 | 294 000 | 137 000 | 1 720 000 |
| 600 | 9 000 | 284 000 | 66 300 | 1 204 740 |

WHITE LIGHT LUMINAIRE FOR EVERYDAY ACTIVITIES THAT REGENERATES THE RETINA OF THE EYE IN REAL TIME, DAMAGED BY BLUE LIGHT

FIELD OF TECHNOLOGY

Luminaires for daily use with retinal repair effect

STATE OF THE ART

As shown in number of scientific reviews and publications, the use of red light for general treatment is well known. Red light is used to treat psychological conditions such as seasonal depression, as well as to treat wounds or for brain treatment. The treatment of the retina with red light is the subject of many papers, for example "Is light with lack of red spectral components a risk factor for age-related macular degeneration (AND)?", SCHIERZ, Christoph. CIE x046: 2019 Proceedings of the 29th CIE SESSION Washington DC, USA, Jun. 14-22, 2019. 2019. The paper summarizes the harmful effects of blue light and its association with age-related macular degeneration, as well as the possibilities of its treatment with red light. The paper itself concludes by stating, among other things, that:

Despite the fact that many papers state the harmful effects of blue light and the healing effects of red light, it is not possible to take a clear position on the issue, because even individual papers show inconsistent results.

There is no known ideal "healthy" ratio between the intensity of blue and red light when combined. The papers mainly study the effect of each color area separately, or in sequence, rather than combination thereof.

The implementation of the knowledge about blue and red light in everyday life is not yet available—this statement beautifully describes the state of the art.

Other papers are, for example, Photobiomodulation for the treatment of retinal diseases: a review, GENEVA, Ivayla I. International journal of ophthalmology, 2016, 9.1: 145 or Red light of the visual spectrum attenuates cell death in culture and retinal ganglion cell death in situ, DEL OLMO-AGUADO, Susana; NÚÑEZ-ÁLVAREZ, Claudia; OSBORNE, Neville N. Acta Ophthalmologica, 2016, 94.6: e481-e491, or Mitochondrial signal transduction in accelerated wound and retinal healing by near-infrared light therapy, EELLS, Janis T., et al. Mitochondrion, 2004, 4.5-6: 559-567.

Extending the light spectrum and increasing the intensity in the red area is offered by most grow lights, including LEDmeGROW, Kindle Grow Lights or Vova. These light sources try to simulate the plants natural radiation and are usually enriched with more intense blue and red areas.

As far as the patent documents are concerned, the combination of a white LED source and a red LED source is already known, either to increase the CRI or to change the chromaticity temperature. A representative document is for example document WO2011143907A1, which describes a light source combining a white LED source and a red LED source to increase the CRI of the resulting light source. This patent constitutes the general state of the art in the sense of combining a white and a red source to increase the CRI.

Another document is for example CN101540362A, which describes a warm white light source combining a white LED source and a red LED. Similar to document WO2011143907A1, it forms the state of the art in the sense of combining a white and a red source, but for a different purpose—to produce warm white.

The state-of-the-art document is also WO2014013462, which describes a light source with an adjustable chromaticity temperature that includes a white LED source, a blue LED source and a red LED source, and a luminophore that converts at least the white LED source to a lime source. Like the referenced documents, this document describes light for a purpose other than retinal repair.

DESCRIPTION OF THE INVENTION

A luminaire has been created that provides an immediate reparative function for the eye's retina, which is exposed to dangerous blue light hazard in everyday life.

The repair itself is provided by the red component of the light in the 660 nm to 680 nm range, but when added to a conventional white LED chip with a chromaticity temperature of 4000 K and a CRI of 80 to 90, it causes a pinkish tint to the emitted light, which in the vast majority of applications is not desirable for the user experience.

Therefore, the model of the luminaire with the reparative component was first rejected by the Applicant. By mistake, however, one of the Inventors combined a reparative red LED chip with a white LED chip with a chromaticity temperature of 2700 K and a CRI of 98 and surprisingly it was found that there is no pink tint to the emitted light but rather an intensification of the warm white light, inducing a relaxing atmosphere. This finding prompted the Applicant to investigate what caused the light with a much higher proportion of the red spectral component to be unaffected by the further addition of the reparative red chip also to transition to pink. As a result, it was subsequently found that the proportion of the green spectral component in the 490 to 570 nm range, once it exceeds a certain threshold, the emitted light cannot buffer the addition of any further color spectral component. Instead, it causes the breakdown of the emitted white light into its individual components, according to the predominance of each. For example, a luminaire consisting of white LED chips with a CCT of 4000 K and a CRI of 98 was found to have a pinking of the emitted light when a red LED chip with 0.48% LUX was added to the white chips, see Spectrum A), as the proportion of the green component of the spectrum exceeded the threshold of 1.6 relative to the proportion of the blue component.

For a luminaire assembled from white LED chips of CT 4000 K and CRI 98 with the addition of blue chips with a peak at 475 nm and a 3.9% LUX contribution relative to the white chips and turquoise LED chips with a peak at 495 nm and a 9.54% LUX contribution relative to the white chips and lime chip, with predominant emitted wavelengths 490 to 570 nm, the emitted light was strongly green (see Spectrum D). However, adding the blue component to a ratio of blue to green of 1:1.6 resulted in the emitted light becoming white again. Thus, only by tuning the ratio between blue and green to values of 1:1.6 at most; as soon as the proportion of green increases (see spectrum D2) above this limit, the addition of any color compared to white light will visibly change the hue.

Another observed phenomenon was found in luminaires assembled from warm white LED chips with a CCT of 2700 K and a CRI of 98, which in itself emits a relatively warm white light and was therefore expected to turn the emitted light pink. To great surprise, however, this did not happen. A wonderfully relaxing warm white radiant luminaire was constructed that showed not a hint of pinkness. It was later found that the ratio of the green spectral component to the red spectral component also plays a decisive role. To be exact, the ratio of green to red is 1:3 and higher. Thus, for example, one part of green and at least 3 parts of red component. Then the addition of the reparative red LED chip is so-called buffered to ensure that the source is still warm white.

Furthermore, the findings confirm the difference between the spectra of D) and D2). Spectrum D) represents a prototype luminaire assembled from white LED chips with CCT 4000 K and CRI 98, pro-cognitive blue LED chips, pro-cognitive turquoise LED chips, green LED chips and red reparative chips. By subjective testing, this spectrum was found to be significantly green by all assessors. However, the moment extra blue LED chips (now represented by the D2 spectrum) are added to this prototype luminaire, the ratio of the green spectral component to the blue spectral component drops below 1.6, to 1.4 to be precise, and the emitted light ceases to be affected by the high proportion of green and the luminaire emits white light.

Such composed luminaires were subjected to in vitro testing of their effect on retinal cells of the eye, precisely cell viability, mitochondrial membrane depolarization and oxygen radical production by irradiation of R28 tissue culture. Prototypes of luminaires CH), D2), sole blue LED chips and white LED chips 4000 K, CRI 98 were tested.

It has been found that the blue LED chips alone significantly damage these cells, reducing their viability to 64% compared to controls in the dark. The white LED chips damage the cells less, their viability is reduced to 82% compared to a control set of cells that were cultured in the dark, but still quite strongly considering that we as users of LED lighting are constantly exposed to this light radiation. The prototype luminaire D2), which has a pro-cognitive effect, i.e. contains a relatively high proportion of blue spectral component, shows very favorable results and during its application there is no damage to retinal cells and these samples show a slightly better condition compared to the control set of cells, exactly by 13%. Even better result is that the prototype luminaire CH), which contains a low proportion of blue spectral component, not only does not damage the retinal cells, but their vitality is higher than the control set of cells cultivated in the dark by 32%.

Similarly, measurements of mitochondrial membrane depolarization were also compared by observing the effect of light on mitochondrial damage. The vitality of mitochondria is significantly increased by the new real-time regenerating luminaires, compared to the control set of cells cultured in the dark, the vitality under the influence of the prototype luminaire D2 is exactly 28% higher and the vitality of cultured retinal cells under the influence of the prototype luminaire CH is 100% higher. In contrast, the amount of healthy vital mitochondria is 48% and 22% lower under the influence of blue LED chips and white LED chips compared to the control.

This leads to the amazing conclusion that under the pleasant illumination of a warm white color with a CCT of 2486 K, which has a high color rendering fidelity, CRI 95.6, the retinal cells damaged earlier are also repaired.

It was further found and documented in Example 6A that the effect of blue light and red light is also significant for the growth or division of retinal lineage R28 cells. The quantitative difference of living cells was monitored over time under the influence of illumination from blue, white, D2 and CH luminaires. The blue light caused rapid apoptosis and, on the contrary, the red light components neutralized the effect of the blue light to ensure an increase in cell vitality, which resulted in significant cell proliferation in a relatively short time. The condition of the cells was monitored until the collapse of the sample set under blue light, i.e. for 600 minutes. Cells under the CH luminaire, i.e. warm white light with a regenerative component, enjoyed high vitality, their number increased from $1*10^5$ to $1.8*10^6$, then nutrient depletion occurred as the experiment was performed in a seeded manner. Another finding is that the pro-cognitive luminaire D2 never causes damage to the retina of the eye despite the high proportion of the blue component with the addition of the red spectral component from the 670 to 680 nm region. On the contrary, the impact is still regenerative.

The amazing and surprising conclusion is that the simple use of the luminaire according to the present invention, at least the white LED chip together with the red chip, will probably provide regeneration of the retinal cells of the eye.

In addition to the luminaires according to the present invention, Example 6B also investigated the effect of the most commonly used pro-cognitive luminaires today, which also attempt to balance the spectrum of the emitted light. Luminaires with the following parameters were tested:

power density ($\lambda$=480 nm)=240 µW/cm², power density ($\lambda$=670 nm)=98 µW/cm², I=40-60 mA Nasli LED: LED 6500K CRI 93 (primary energy $\lambda \approx 450$ nm)

Sunlike: LED 4000K CRI 95 (primary energy $\lambda \approx 420$ nm)

LED 480: 4000 K CRI 80 (primary energy $\lambda \approx 450$ nm)

D2 LED 4900K CRI 95 with 670 nm (primary energy $\lambda \approx$ multi)

and compared with the pro-cognitive luminaire D2 according to the present invention, to which the commercial luminaires are the closest. All these luminaires caused cell apoptosis after about 200 minutes of illumination. On the contrary, the D2 luminaire ensured that the number of live cells increased again to the original values after a drop to half of the seeded amount of cells. The subsequent drop is already expected and seems to follow the drop of nutrients in the sample.

Terms Used

Blue spectral component: the light source emits light energy in the wavelength range 400 to 490 nm Green spectral component: the light source emits light energy in the wavelength range 490 to 570 nm Red spectral component: the light source emits light energy in the wavelength range 570 to 780 nm Pro-cognitive Blue LED chip: LED chip emitting light energy in the range 470 to 480 nm Pro-cognitive Turquoise LED chip: LED chip emitting light energy in the range 490 to 500 nm Blue LED chip: LED chip emitting light energy in the range at least 420 to 460 nm Red reparation LED chip: LED chip emitting light energy with a maximum at the wavelength $\lambda$=670 to 680 nm.

Green LED chip: LED chip emitting light energy in the range at least 500 nm to 660 nm with a maximum at $\lambda$=500 to 580 nm.

Composition of Assembled Prototype Luminaires:

A) A light source luminaire with a CCT of 3797 and a CRI of 97.1 assembled from white LED chips with a CCT of 4110 K and a CRI of 97.5 with a relative input power of 95.32% and a proportion of the illuminance in LUX of 99.52% and red reparative LED chips with a relative input power of 4.68% and a proportion of LUX of 0.48%.

B) A light source luminaire with a CCT of 3741 and a CRI of 88.4 assembled from white LED chips with a CCT of 4021 K and a CRI of 85.2 with a relative input power of 89.61% and a proportion of the illuminance in LUX of 99.16% and red reparative LED chips with a relative input power of 10.39% and a proportion of LUX of 0.84%.

C) A light source luminaire with a CCT of 4681 and a CRI of 86.5 assembled from white LED chips with a CCT of 4108 K and a CRI of 97.7 with a relative input power of 72.13% and a proportion of the illuminance in LUX of 86.15%, pro-cognitive blue LED chips with relative input power of 12.12% and a proportion of the illuminance in LUX of 3.9%, pro-cognitive turquoise LED chips with relative input power of 12.37% and a proportion of the illuminance in LUX of 9.54%, and red reparative LED chips with a relative input power of 3.37% and a proportion of LUX of 0.40%.

D) A light source luminaire with a CCT of 4583 and a CRI of 92.6 assembled from white LED chips with a CCT of 4116 K and a CRI of 97.6 with a relative input power of 69.29% and a proportion of the illuminance in LUX of 70.28%, pro-cognitive blue LED chips with relative input power of 7.58% and a proportion of the illuminance in LUX of 2.14%, pro-cognitive turquoise LED chips with relative input power of 6.15% and a proportion of the illuminance in LUX of 4.05%, green LED PC lime chips with relative input power of 12.51% and a proportion of the illuminance in LUX of 23.04%, and red reparative LED chips with a relative input power of 4.68% and a proportion of LUX of 0.48%.

D2) A light source luminaire with a CCT of 4865 and a CRI of 96 assembled from white LED chips with a CCT of 4116 K and a CRI of 97.6 with a relative power input of 66.25% and a proportion of the illuminance in LUX of 69.83%, blue 440 nm LED chips with a relative power input of 2.93% and a proportion of LUX of 0.22%, pro-cognitive blue 475 nm LED chips with a relative power input of 8.7% and a LUX proportion of 2.55%, pro-cognitive turquoise 495 nm LED chips with a relative power input of 5.88% and a LUX proportion of 4.02%, green PC lime LED chips with a relative power input of 11.96% and a LUX proportion of 22.9% and red reparative LED chips with a relative power input of 4.28% and a LUX proportion of 0.48%.

E) A light source luminaire with a CCT of 4374 and a CRI of 89.6, assembled from violet LED chips with a relative power input of 24.38% and a LUX illuminance proportion of 12.63%, blue 440 nm LED chips with a relative power input of 3.24% and a LUX proportion of 0.23%, pro-cognitive blue 475 nm LED chips with a relative power input of 13.07% and a LUX proportion of 3.23%, pro-cognitive turquoise 495 nm LED chips with a relative power input of 13.5% and a LUX proportion of 7.65%, green PC lime LED chips with a relative power input of 37.75% and a LUX proportion of 71.81%, orange PC amber LED chips with a relative power input of 3.15% and a LUX proportion of 3.93% and red reparative LED chips with a relative power input of 4.91% and a LUX proportion of 0.51%.

C) A light source luminaire with a CCT of 5120 and a CRI of 95.1 assembled from white LED chips with a CCT of 5141 K and a CRI of 96.8 with a relative input power of 96.92% and a proportion of the illuminance in LUX of 98.76%, pro-cognitive blue LED chips with relative input power of 0.97% and a proportion of the illuminance in LUX of 0.52%, pro-cognitive turquoise LED chips with relative input power of 0.31% and a proportion of the illuminance in LUX of 0.41%, and red reparative LED chips with a relative input power of 1.8% and a proportion of LUX of 0.32%.

G) A light source luminaire with a CCT of 4932 and a CRI of 98.6 assembled from white LED chips with a CCT of 5141 K and a CRI of 96.8 with a relative input power of 100% and a proportion of the illuminance in LUX of 100%.

H) A light source luminaire with a CCT of 4169 and a CRI of 92.4 assembled from white LED chips with a CCT of 4110 K and a CRI of 97.5 with a relative input power of 89.81% and a proportion of the illuminance in LUX of 99.10%, and blue LED chips with relative input power of 4.4% and a proportion of LUX of 0.47%, and red reparative LED chips with a relative input power of 4.40% and a proportion of LUX of 0.47%.

CH) A light source luminaire with a CCT of 2486 and a CRI of 95.6 assembled from white LED chips with a CCT of 2653 K and a CRI of 96.2 with a relative input power of 95.23% and a proportion of the illuminance in LUX of 99.31% and red reparative LED chips with a relative input power of 4.77% and a proportion of LUX of 0.69%.

I) A light source luminaire with a CCT of 2725 and a CRI of 88.8 assembled from white LED chips with a CCT of 2653 K and a CRI of 96.2 with a relative input power of 85.31% and a proportion of the illuminance in LUX of 98.51%, blue LED chips with relative input power of 8.25% and a proportion of LUX of 0.73%, and red reparative LED chips with a relative input power of 6.44% and a proportion of LUX of 0.76%.

The advantage of the luminaire for everyday activities that regenerates the retina of the eye in real time is that it is possible to use light sources with a higher proportion of the blue spectral component excited at lower wavelengths, i.e. 440 nm, 420 nm or even 400 nm because under the set conditions of the ratio of the spectral components of blue, green and red such a luminaire immediately neutralizes the negative dangerous effects of blue light.

The ratios of luminous intensities in lx were used only for comparison between the spectra in the proposed constant measurement system.

SUMMARY

White light luminaire for everyday activities that regenerates the retina of the eye in real time, damaged by blue light, contains at least one white LED chip with chromaticity temperature of 2100 K to 5000 K, at least one red chip with the maximum of the radiated energy at the wavelength $\lambda=670$ to 680 nm, whereas the ratio between the blue spectral component from the wavelength range 400 to 490 nm and the green spectral component from the wavelength range 490 to 570 nm is 1:1.6 max., or the ratio between the green spectral component from the wavelength range 490 to 570 nm and the red spectral component from the wavelength range 570 to 780 nm is 1:3 min.

Preferably, the ratio between the blue spectral component from the wavelength range 400 to 490 nm and the green spectral component from the wavelength range 490 to 570 nm is 1:1 to 1.6.

Preferably, the ratio between the green spectral component from the wavelength range 490 to 570 nm and the red spectral component from the wavelength range 570 to 780 nm is 1:3 to 5.

Preferably is the blue chip overlaid with the luminophore is a white LED chip having a chromaticity temperature of 2700 to 4000 K and a CRI of at least 90.

Preferably, the ratio between the spectral components is expressed in mW/m$^2$.

The white light luminaire preferably comprises a blue chip with peak emission in the wavelength range λ=420 to 450 nm.

The white light luminaire preferably comprises a pro-cognitive blue LED chip with peak emission in the wavelength range λ=470 to 480 nm and a pro-cognitive turquoise chip with peak emission in the wavelength range λ=490 to 500 nm.

The white light luminaire preferably comprises a green chip having an emitted light energy in the range of at least 500 nm to 660 nm with a maximum at λ=500 to 580 nm.

SUMMARY OF PRESENTED DRAWINGS

Figure 13A:
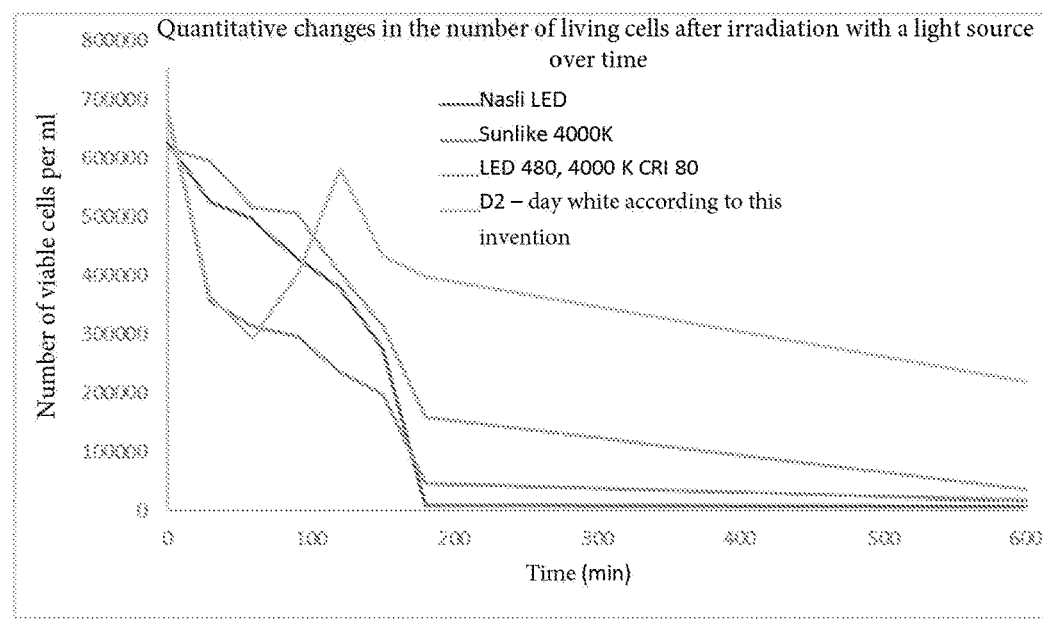
Figure 13B:
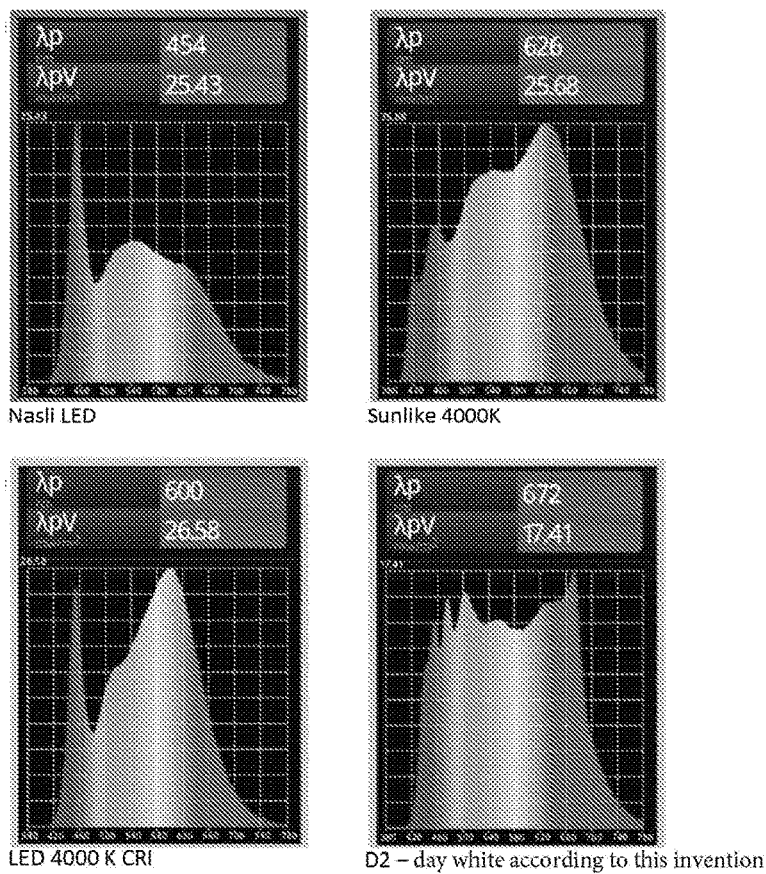

FIG. 1.1 Individual spectral components, luminaire A)
FIG. 1.2 Individual spectral components, luminaire B)
FIG. 1.3 Individual spectral components, luminaire C)
FIG. 1.4 Individual spectral components, luminaire D)
FIG. 1.5 Individual spectral components, luminaire D2)
FIG. 1.6 Individual spectral components, luminaire E)
FIG. 1.7 Individual spectral components, luminaire F)
FIG. 1.8 Individual spectral components, luminaire G)
FIG. 1.9 Individual spectral components, luminaire H)
FIG. 1.10 Individual spectral components, luminaire CH)
FIG. 1.11 Individual spectral components, luminaire I)
FIG. 2 Comparison of individual spectra and properties of light
FIG. 3.1 Individual components of spectra with indicated spectra of individual chips A)
FIG. 3.2 Individual components of spectra with indicated spectra of individual chips B)
FIG. 3.3 Individual components of spectra with indicated spectra of individual chips C)
FIG. 3.4 Individual components of spectra with indicated spectra of individual chips D)
FIG. 3.5 Individual components of spectra with indicated spectra of individual chips D2)
FIG. 3.6 Individual components of spectra with indicated spectra of individual chips E)
FIG. 3.7 Individual components of spectra with indicated spectra of individual chips G)
FIG. 3.8 Individual components of spectra with indicated spectra of individual chips H)
FIG. 3.9 Individual components of spectra with indicated spectra of individual chips CH)
FIG. 3.10 Individual components of spectra with indicated spectra of individual chips I)
FIG. 4.1 Individual components of spectra with ratios of spectral components A)
FIG. 4.2 Individual components of spectra with ratios of spectral components B)
FIG. 4.3 Individual components of spectra with ratios of spectral components CH)
FIG. 4.4 Individual components of spectra with ratios of spectral components D2)
FIG. 5 Identification of components of individual luminaires A) to I)
FIG. 6 Luminaire prototypes A) to I) and their assessment
FIG. 7 Color ratios of luminaires A), B), H), CH), D2)
FIG. 8 Testing of luminaires A), B), CH), D2) on tissue cultures according to Example 5B FIG. 9.1 Testing of luminaries A), B), CH), D2) on tissue cultures according to Example 5C, the extent of mitochondrial damage after light treatment
FIG. 9.2 Testing of luminaries A), B), CH), D2) on tissue cultures according to Example 5C, the extent of mitochondrial damage after light treatment
FIG. 9.3 Testing of luminaries A), B), CH), D2) on tissue cultures according to Example 5C, the extent of mitochondrial health after light treatment
FIG. 9.4 Testing of luminaries A), B), CH), D2) on tissue cultures according to Example 5C, the extent of mitochondrial health after light treatment
FIG. 10 Testing of luminaires A), B), CH), D2) on tissue cultures according to Example 5D
FIG. 11 Light outputs of the blue and red components of the luminaires used for testing according to Example 5
FIG. 12A Table showing number of living cells over time after exposure to various light sources
FIG. 12B Graph showing quantitative changes in number of living cells after irradiation with various light sources over time
FIG. 13A Graph showing quantitative changes in number of living cells after irradiation with various light sources over time
FIG. 13B Spectra showing properties of Nasil LED. Sunlike 4000K. LED 4000 K CRI 80, and D2 day white according to the present invention

EXAMPLES OF INVENTION EXECUTION

Example 1 Prototype of Luminaire A

A prototype luminaire was assembled, with PCBs populated with 16 white LED chips of CCT 4110 K and CRI 97.5, with per-chip input power of 360 mW, illuminance 636.6 lx, λp 455 nm, λpV 12.22 mW/m$^2$, where for these white chips the total power input was 5760 mW and the total illuminance was 10185.6 lx and 1 red reparative LED chip with per-chip power input of 282.5 mW, illuminance 48.75 lx, λp 677 nm, λpV 54.85 mW/m$^2$. The total input power of the luminaire was thus 6042.5 mW and the total illuminance was 10234.35 lux. Thus, the white chips accounted for a relative input power of 95.32% and a relative illuminance of 99.52%, and the red reparative chip accounted for a relative input power of 4.68% and a relative illuminance of 0.48% of the entire luminaire.

The prototype luminaire thus constructed was subjected to a subjective assessment, with the conclusion that the luminaire emits light of a pleasant white color, but is perceived by all assessors as pink. Furthermore, the perceived CCT was assessed as neutral white. It was therefore concluded that the light emitted by this luminaire has a perceived chromaticity temperature of neither cold nor warm, but neutral white. That means that the addition of the red reparative LED chip did not provide a warmer shade of white but caused it to turn pink.

The ratio of the spectral components of blue and green was 1:1.7, which is already beyond the edge of light buffering, and therefore the addition of the red LED chip does not blend/integrate into the existing light, but has a completely independent and separate effect on the subjective assessment of the light shade.

Example 2 Prototype of Luminaire B

A prototype luminaire was assembled, with PCBs populated with 16 white LED chips of CCT 4110 K and CRI 85.2, with per-chip input power of 352.58 mW, illuminance 886.4 lx, λp 455 nm, λpV 16.27 mW/m², where for these white chips the total power input was 5641.28 mW and the total illuminance was 14182.4 lx and 3 red reparative LED chips with per-chip power input of 218 mW, illuminance 40.17 lx, λp 676 nm, λpV 45.45 mW/m². The total input power of the luminaire was thus 6295.28 mW and the total illuminance was 14302.91 lux. Thus, the white chips accounted for a relative input power of 89.61% and a relative illuminance of 99.16%, and the red reparative chips accounted for a relative input power of 10.39% and a relative illuminance of 0.84% of the entire luminaire.

The prototype luminaire thus constructed was subjected to a subjective assessment, with the conclusion that the luminaire emits light of a pleasant white color without any color tinge. Furthermore, the perceived CCT was assessed as neutral white. It was therefore concluded that the light emitted by this luminaire has a perceived chromaticity temperature of neither cold nor warm, but neutral white. That means that the addition of the red reparative LED chip did not provide a warmer shade of white neither caused it to turn pink.

The ratio of the spectral components of blue and green was 1:1.6, the upper limit of the light buffering capacity, and the addition of the red LED chip blended into the existing light without affecting it.

Example 3 Prototype of Luminaire CH

A prototype luminaire was assembled, with PCBs populated with 16 white LED chips of CCT 2653 K and CRI 96.2, with per-chip input power of 360 mW, illuminance 511.1 lx, λp 635 nm, λpV 12.55 mW/m², where for these white chips the total power input was 5760 mW and the total illuminance was 8177.6 lx and 2 red reparative LED chips with per-power input of 144.2 mW, illuminance 28.5 lx, λp 675 nm, λpV 33.21 mW/m². The total input power of the luminaire was thus 6048.4 mW and the total illuminance was 8234.6 lux. Thus, the white chips accounted for a relative input power of 95.23% and a relative illuminance of 99.31%, and the red reparative chip accounted for a relative input power of 4.77% and a relative illuminance of 0.69% of the entire luminaire.

The prototype luminaire thus constructed was subjected to a subjective assessment, with the conclusion that the luminaire emits light of a pleasant warm white color without any color tinge. Furthermore, the perceived CCT was assessed as warm white. It was therefore concluded that the light emitted by this luminaire has a perceived chromaticity temperature of warm white. That means that the addition of the red reparative LED chip in this case did not interfere with the color of the majority warm white LED chip and only blended with the white LED chip.

The ratio of the spectral components of blue and green was 1:2.8, which is beyond the limit of light buffering and therefore the second condition applies and that is the minimum ratio of the spectral components of green and red, which is at least 1:3, in this particular case 1:4, so the color of the light is not affected by the addition of the red LED chip.

Example 4 Prototype of Luminaire D2

A prototype luminaire was assembled, whose PCBs were populated with 16 white LED chips of CCT 4116 K and CRI 97.6, with per-chip power of 291.06 mW, illuminance 546.4 lx, λp 455 nm, λpV 10.64 mW/m², when the total power consumption of these white chips was 4656.96 mW and the total illuminance was 8742.4 lx, one blue monochromatic LED chip with a wavelength of 440 nm with per-chip input power of 205.92 mW, an illuminance of 27.44 lx, λp 437 nm, λpV 67.91 mW/m², three blue monochromatic LED chips with a wavelength of 475 nm with per-chip input power of 203.76 mW, illuminance 106.4 lx, λp 474 nm, λpV 34.48 mW/m², two turquoise monochromatic LED chips with a wavelength of 495 nm with per-chip power 206.64 mW, illuminance 251.9 lx, λp 498 nm, λpV 26.66 mW/m², three green PC LED chips with per-chip power of 280.17 mW, illuminance of 955.5 lx, λp 543 nm, λpV 17.45 mW/m², and two red reparative LED chips with per-chip power of 150.48 mW, illuminance of 30.13 lx, λp 675 nm, λpV 34.12 mW/m². The total input power of the luminaire was thus 7028.91 mW and the total illuminance was 12519.6 lx. The white chips accounted for a relative power input of 66.25% and a relative illuminance of 69.83%, and the red reparative chips accounted for a relative power input of 60.26% and a relative illuminance of 0.48% of the entire luminaire.

The prototype luminaire thus constructed was subjected to a subjective assessment, with the conclusion that the luminaire emits light of a pleasant white color without any color tinge. Furthermore, the perceived CCT was assessed as colder white. It was therefore concluded that the light emitted by this luminaire has a perceived chromaticity temperature of colder white. That means that the addition of the red reparative LED chip in this case did not interfere with the color of the white LED chip or other colored LED chips and only blended with the light emitted by the other LED chips.

The ratio of the spectral components of blue and green was 1:1.4, which is within the limits of light buffering, i.e. the color of the light is not affected by the addition of the red LED chip.

Example 5A

The prototype luminaires produced according to Examples 1 to 4 were tested on R28 tissue culture (Retinal Cell Line, Kerafast).

The cells were pre-grown in a high concentration of glucose and pyruvate, Dulbecco's Modified Eagle Medium—DMEM, supplemented with 3.3% v/v sodium bicarbonate solution, 10% FBS, 1% MEM non-essential amino acids, 1% MEM vitamins, 1% glutamine and 1% gentamicin in a 5% $CO_2$ atmosphere at 37° C.

A 0.1 ml of suspension of cultivated R28 cells at a concentration of 80,000 cells/ml was pipetted into the wells of a 96-well plate and allowed to settle for 24 hours before the cells were exposed to different light treatments, FIG. 11:

CH—Treatment with the CH luminaire—warm white with added red component, blue spectral component with the output of 0.7 mW/m², red spectral component with the output of 2.6 mW/m²

D2—Treatment with the D2 luminaire—day white, procognitive with added red component, blue spectral component with the output of 1.9 mW/in, red spectral component with the output of 1.9 mW/m²

Blue—Treatment with the luminaire emitting blue light 440 nm, blue spectral component with the output of 23.5 mW/m², red spectral component with the output of 0.1 mW/m²

White—Treatment with the luminaire emitting white light CCT 4000 K and CRI 98, blue spectral component with the output of 10.6 mW/m², red spectral component with the output of 9.3 mW/m²

Dark—Dark treatment

The temperature was maintained at 37° C. throughout the testing, with an atmosphere of 5% $CO_2$.

Individual luminaires were measured using a spectrophotometer.

The cells were subjected to the tests according to Example 5B to 5):

Example 5B Viability of Cells

The viability of cells was assessed using the reduction test. The cells of the 96-well plates were subjected to the respective CH, D2, Blue, White and Dark light treatment for 12 hrs. The dark treatment (T) was chosen as a control. Subsequently, (4,5-dimethylthiazol-2-yl)-2,5-diphenyltetrazolium bromide (MTT) was added to the wells at a final concentration of 0.5 mg/ml and the cells were incubated for 75 min at 37° C. The medium was then removed and MTT was reduced by addition of 100 µl dimethyl sulfoxide (DMSO) into each well. The plates were stirred for 10 minutes, and then the optical density was measured in individual wells at wavelength of 570 nm. {The average absorbance of the control (T) in each experiment was defined as 100% and all measurements of light-treated samples were referenced to it. The results are shown in FIG. 8. It can be seen that Blue and White light caused damage to the cells, resulting in their lower absorbance. On the other hand, CH and D2 exhibit a supportive effect on cell growth.

Example 5C Mitochondrial Depolarization

To assess mitochondrial membrane depolarization, cells were subjected to the respective light treatments of CH, D2, Blue, White, and Dark for 12 hrs. The dark treatment (T) was chosen as a control. Then, medium was removed from the cultures and the cells were incubated with the JC-1 dye, a final concentration of 2 µg/ml for 30 minutes. Then, detection was carried out at 590 and 530 nm. The dye accumulated in the mitochondria of healthy cells appears as red/orange fluorescence at 590 nm. The dye accumulated in the depolarized mitochondrial membrane of damaged cells appears as green fluorescence at 530 nm. From the fluorescence microscope images, image analysis was carried out and the average red and green fluorescence of the control was set to be 100%. The results are shown in FIG. 9. FIGS. 9.1 and 9.2 show the extent of mitochondrial damage, where the maximum damage is caused by the Blue luminaire. In terms of damage the White luminaire followed and the samples illuminated by CH and D2 luminaires were without damage. In contrast, FIGS. 9.3 and 9.4 show the extent of mitochondrial vitality support, with mitochondria showing higher vitality after illumination with C1 and D2 luminaires than after dark treatment.

Example 5D Reactive Oxygen Species (ROS) Production and Response to them

ROS production: The cells were subjected to the respective CH, D2, Blue, White and Dark light treatment for 12 hrs. The dark treatment (T) was chosen as a control. The medium was then removed from the cultures and the cultures were rinsed twice with fresh medium and then incubated with dihydroethidium, final concentration 40 µM, for 20 min. The solution was removed, and the cells were rinsed twice with fresh medium. Immediately afterwards, phase fluorescence/contrast microscopy images were taken. In the case of ROS production, red fluorescent chromatin in the nuclei is visible in the images. The images were then subjected to image analysis, and the mean red fluorescence of the control was set to 0. The results are shown in FIG. 10. The ROS production is caused by the presence of the blue component of the light spectrum. Not surprisingly, the samples illuminated by the Blue luminaire show the highest ROS, followed by the White luminaire and the D2 luminaire. The CH luminaire shows the minimum ROS production.

Example 6

R28 tissue culture cells (Retinal Cell Line, Kerafast) were thawed at laboratory temperature for 15 min. Subsequently, the cells were pipetted into 5 ml DMEM+ medium and centrifuged for 5 min. The cell pellet was suspended in 10 ml of DMEM+ medium using a vortex and the suspension was incubated in an incubator at 37° C. and 5% $CO_2$ for two days.

After two days of incubation, the cells were passaged. The cells were rinsed by 1 ml of EDTA. Next, 1 ml of EDTA and 1 ml of trypsin were added and the culture bottle thus prepared was incubated at laboratory temperature for 5 minutes. Then 5 ml of fresh DMEM+ medium was added and the solution was stirred using a vortex. Half of the suspension was pipetted into a new culture bottle and fresh DMEM+ medium was added to both bottles to a final volume of 20 ml. The cultivation bottles thus prepared were placed in the incubator again, and incubated at 37° C. and 5% $CO_2$ for three days. The initial concentration after cultivation was approximately 519 000 to 579 000 cells per ml.

The cells were then pipetted into individual wells of a 12-well plate. The cells were checked every day under a microscope for their growth. Subsequently, after three days, cells were placed in a 37° C. and 5% $CO_2$ incubator and exposed to the various light sources specified below up to a light source distance of 400 mm from the well plate. Cells exposed to the light emitter were sequentially sampled at different time points. At each time point, cells were collected from one well, processed, and their concentration, or number of live cells, was measured. The results were plotted in a table and graph and are shown in FIGS. 12A, 12B and 13A, 13B.

Part A) Light sources according to the present invention, FIGS. 12A and 12B:
  Blue, 440 nm, according to the present invention
  White, CCT 4000 K and CRI 98, according to the present invention
  Day white—D2—according to the present invention
  Warm white—CH—according to the present invention Part B) Light source according to the present invention, compared with the start of the art, FIGS. 13A and 13B:
  Nasli LED,
  Sunlike 4000 K,
  LED 4000 K CRI 80,
  Warm white—CH—according to the present invention The specific power of all light sources was normalized to $\lambda_{480\ nm} = 240\ \mu W/cm^2$, to the point of maximum sensitivity of the melanopic receptors of the non-visual system responsible for the body's day/night synchronization.

INDUSTRIAL APPLICABILITY

Illumination with reparative effects for the eye retina

The invention claimed is:

1. A white light luminaire, wherein a perceived CCT of a white light emitted from the luminaire is without any non-white color tinge, for everyday activities that regenerates retinal cells and promotes cell proliferation of the eye in real time, damaged by blue light, characterized in that it contains at least one white LED chip with chromaticity temperature of 2100 K to 5000 K, at least one red chip with a maximum of a radiated energy at a wavelength $\lambda$=670 to 680 nm,
   whereas a ratio between a blue spectral component from a wavelength range 400 to 490 nm and a green spectral component from a wavelength range 490 to 570 nm is 1:1.6 max, or
   a ratio between a green spectral component from a wavelength range 490 to 570 nm and a red spectral component from a wavelength range 570 to 780 nm is 1:3 min.

2. The white light luminaire for everyday activities that regenerates the retina of the eye in real time, damaged by blue light according to claim 1 characterized in that the ratio between the blue spectral component from the wavelength range of 400 to 490 nm and the green spectral component from the wavelength range of 490 to 570 nm is 1:1 to 1.6.

3. The white light luminaire for everyday activities that regenerates the retina of the eye in real time, damaged by blue light according to claim 1 characterized in that the ratio between the green spectral component from the wavelength range of 490 to 570 nm and the red spectral component from the wavelength range of 570 to 780 nm is 1:3 to 5.

4. The white light luminaire for everyday activities that regenerates the retina of the eye in real time, damaged by blue light according to claim 2, characterized in that white LED chip is a blue chip covered by the luminophore with chromaticity temperature of 2700 K to 4000 K and CRI of at least 90.

5. The white light luminaire for everyday activities that regenerates the retina of the eye in real time, damaged by blue light according to claim 1 characterized in that the ratio between the spectral components is expressed in mW/m$^2$.

6. The white light luminaire for everyday activities that regenerates the retina of the eye in real time, damaged by blue light according to claim 1 characterized in that it contains a blue LED chip with emission peak in a wavelength range $\lambda$=420 to 450 nm.

7. The white light luminaire for everyday activities that regenerates the retina of the eye in real time, damaged by blue light according to claim 1 characterized in that it contains a pre-cognitive blue LED chip with emission peak in a wavelength range $\lambda$=470 to 480 nm and a pro-cognitive turquoise LED chip with emission peak in a wavelength range $\lambda$=490 to 500 nm.

8. The white light luminaire for everyday activities that regenerates the retina of the eye in real time, damaged by blue light according to claim 1 characterized in that it contains a green chip with emitted light energy in a wavelength range at least 500 to 660 nm with a maximum at $\lambda$=500 to 580 nm.

* * * * *